United States Patent
Tanaka et al.

(10) Patent No.: US 10,351,864 B2
(45) Date of Patent: Jul. 16, 2019

(54) CLONING VECTOR

(71) Applicant: AGC Inc., Chiyoda-ku (JP)

(72) Inventors: Takayuki Tanaka, Chiyoda-ku (JP); Tetsuya Kotani, Chiyoda-ku (JP); Futoshi Hara, Chiyoda-ku (JP)

(73) Assignee: AGC Inc., Chiyoda-ku (JP)

( * ) Notice: Subject to any disclaimer, the term of this patent is extended or adjusted under 35 U.S.C. 154(b) by 0 days.

(21) Appl. No.: 15/850,890

(22) Filed: Dec. 21, 2017

(65) Prior Publication Data

US 2018/0187205 A1 Jul. 5, 2018

Related U.S. Application Data

(63) Continuation of application No. PCT/JP2016/068866, filed on Jun. 24, 2016.

(30) Foreign Application Priority Data

Jul. 2, 2015 (JP) ................. 2015-133781

(51) Int. Cl.
*C12N 15/81* (2006.01)
*C12P 21/00* (2006.01)
*C12N 15/09* (2006.01)

(52) U.S. Cl.
CPC ........... *C12N 15/815* (2013.01); *C12N 15/09* (2013.01); *C12P 21/00* (2013.01)

(58) Field of Classification Search
CPC ................................ C12N 15/81; C12P 21/00
See application file for complete search history.

(56) References Cited

U.S. PATENT DOCUMENTS

2015/0240250 A1 8/2015 Kobayashi et al.

FOREIGN PATENT DOCUMENTS

WO WO 2014/030644 A1 2/2014

OTHER PUBLICATIONS

International Search Report dated Aug. 16, 2016 in PCT/JP2016/068866, filed on Jun. 24, 2016.
Mamoru Yamanishi, et al. "A Genome-Wide Activity Assessment of Terminator Regions in *Saccharomyces cerevisiae* Provides a "Terminatome" Toolbox", ACS Synthetic Biology, vol. 2, 2013, 11 pages, pp. 337-347.
Schizosaccharomyces pombe chromosome I, complete sequence, Database GenBank, Accession No. CU329670.1, http://www.ncbi.nlm.nih.gov/nuccore/CU32970, 2015, 2 pages.

*Primary Examiner* — Antonio Galisteo Gonzalez
(74) *Attorney, Agent, or Firm* — Oblon, McClelland, Maier & Neustadt, L.L.P.

(57) ABSTRACT

The object is to provide an expression vector capable of expressing with a higher expression efficiency a protein derived from a foreign structural gene by genetic engineering using a yeast of the genus *Schizosaccharomyces* as a host, a cloning vector to produce the expression vector, a method for producing the expression vector, a transformant containing an expression cassette of the expression vector, a method for producing the transformant, and a method for producing a protein using the transformant.

A cloning vector comprising a promoter capable of functioning in a yeast of the genus *Schizosaccharomyces*, a cloning site for introducing a foreign structural gene which is located downstream from the promoter and is regulated by the promoter, and ihc2 gene terminator of the yeast of the genus *Schizosaccharomyces*, and an expression vector comprising the promoter, the foreign structural gene and the ihc2 gene terminator.

20 Claims, 5 Drawing Sheets

Specification includes a Sequence Listing.

CLONING VECTOR

This application is a continuation of PCT Application No. PCT/JP2016/068866, filed on Jun. 24, 2016, which is based upon and claims the benefit of priority from Japanese Patent Application No. 2015-133781 filed on Jul. 2, 2015. The contents of those applications are incorporated herein by reference in their entireties.

TECHNICAL FIELD

The present invention relates to an expression vector to produce a transformant using a yeast of the genus *Schizosaccharomyces* as a host, a cloning vector to produce the expression vector, a method for producing the expression vector, a transformant having an expression cassette of the expression vector, a method for producing the transformant, and a method for producing a protein using the transformant. Specifically, it relates to an expression vector which can improve expression efficiency by using a specific terminator, etc.

BACKGROUND ART

Because of their various characteristics, yeasts of the genus *Schizosaccharomyces* represented by *Schizosaccharomyces pombe* (hereinafter sometimes referred to as *S. pombe*) are considered as unicellular eukaryotes closer to higher animal cells and very useful yeasts as a host for expression of foreign structural genes, especially genes derived from higher animals. In particular, they are known to be suitable for expression of genes derived from animals such as human.

In order to express a protein utilizing transcription and translation systems of organisms, an expression cassette which comprises, upstream from a foreign structural gene encoding a heterologous protein, a promoter controlling transcription of the foreign structural gene, and a terminator to release mRNAs obtained by transcription, into a cell as a host cell. It is known that the expression efficiency is influenced by the type of the promotor used. It is possible to express a protein even without a terminator, and the terminator has not been considered important so far. However, in recent years, it is reported that the expression efficiency varies depending upon the type of the terminator used, in a budding yeast *Saccharomyces cerevisiae* (Non-Patent Document 1).

PRIOR ART DOCUMENTS

Non-Patent Documents

Non-Patent Document 1: Yamanishi et al., ACS Synthetic Biology, 2013, vol.2, p.337-347.

DISCLOSURE OF INVENTION

Technical Problem

The object of the present invention is to provide an expression vector capable of expressing with a higher expression efficiency a protein derived from a foreign structural gene by genetic engineering using a yeast of the genus *Schizosaccharomyces* as a host, a cloning vector to produce the expression vector, a method for producing the expression vector, a transformant containing the expression vector, a method for producing the transformant, and a method for producing a protein using the transformant.

Solution to Problem

The present inventors have conducted extensive studies to achieve the above object and as a result, found that the expression efficiency is remarkably improved by using ihc2 gene terminator of a yeast of the genus *Schizosaccharomyces* as compared with a case of using a conventional terminator such as nmt1 terminator, and accomplished the present invention.

That is, the present invention provides the following [1] to [15].

[1] A cloning vector comprising a promoter capable of functioning in a yeast of the genus *Schizosaccharomyces*, a cloning site for introducing a foreign structural gene which is located downstream from the promoter and is regulated by the promoter, and ihc2 gene terminator of the yeast of the genus *Schizosaccharomyces*.

[2] The cloning vector according to the above [1], wherein the ihc2 gene terminator is a region 1 to 625 bp downstream from the 3' end of ihc2 gene ORF (open reading frame).

[3] The cloning vector according to the above [1] or [2], wherein the ihc2 gene is a gene of *Schizosaccharomyces pombe*.

[4] The cloning vector according to any one of the above [1] to [3], wherein the terminator comprises a nucleotide sequence represented by SEQ ID NO:19 or the nucleotide sequence having substitution, deletion or addition of at least one nucleotide, and has a terminator activity.

[5] The cloning vector according to any one of the above [1] to [3], wherein the terminator comprises a nucleotide sequence having at least 80% homology with a nucleotide sequence represented by SEQ ID NO: 19 and has a terminator activity.

[6] An expression vector comprising a promoter capable of functioning in a yeast of the genus *Schizosaccharomyces*, a foreign structural gene which is located downstream from the promoter and is regulated by the promoter, and ihc2 gene terminator of the yeast of the genus *Schizosaccharomyces*.

[7] The expression vector according to the above [6], wherein the ihc2 gene terminator is a region 1 to 625 bp downstream from the 3' end of ihc2 gene ORF (open reading frame).

[8] A method for producing an expression vector, which comprises introducing a foreign structural gene into the cloning site of the cloning vector as defined in any one of the above [1] to [5].

[9] A method for producing an expression vector, which comprises replacing, of an expression vector comprising a promoter capable of functioning in a yeast of the genus *Schizosaccharomyces*, a foreign structural gene which is located downstream from the promoter and is regulated by the promoter, and a terminator other than the following terminator, the terminator with ihc2 gene terminator of the yeast of the genus *Schizosaccharomyces*.

[10] A transformant of a yeast of the genus *Schizosaccharomyces*, comprising an expression cassette containing a promotor capable of functioning in the yeast of the genus *Schizosaccharomyces*, a foreign structural gene which is located downstream from the promoter and is regulated by the promoter, and ihc2 gene terminator of the yeast of the genus *Schizosaccharomyces*.

[11] The transformant according to the above [10], which has an expression vector containing the expression cassette outside its chromosome.

[12] The transformant according to the above [10], which has the expression cassette in its chromosome.

[13] A method for producing the transformant as defined in the above [10], which comprises making an expression vector containing the expression cassette be maintained outside a chromosome of a yeast of the genus *Schizosaccharomyces*.

[14] A method for producing the transformant as defined in the above [10], which comprises introducing an expression vector containing the expression cassette into a chromosome of a yeast of the genus *Schizosaccharomyces*.

[15] A method for producing a protein, which comprises cultivating the transformant as defined in any one of the above [10] to [12], and, from cells or a culture supernatant thereby obtained, recovering a protein encoded by the foreign structural gene.

Advantageous Effect of Invention

According to the cloning vector of the present invention, it is possible to easily produce an expression vector capable of expressing a protein derived from a foreign structural gene with a higher expression efficiency, using a yeast of the genus *Schizosaccharomyces* as a host.

According to the transformant obtained by the expression vector of the present invention, it is possible to produce the foreign protein with a high expression efficiency.

DESCRIPTION OF EMBODIMENTS

[Cloning vector]

Figure 1:
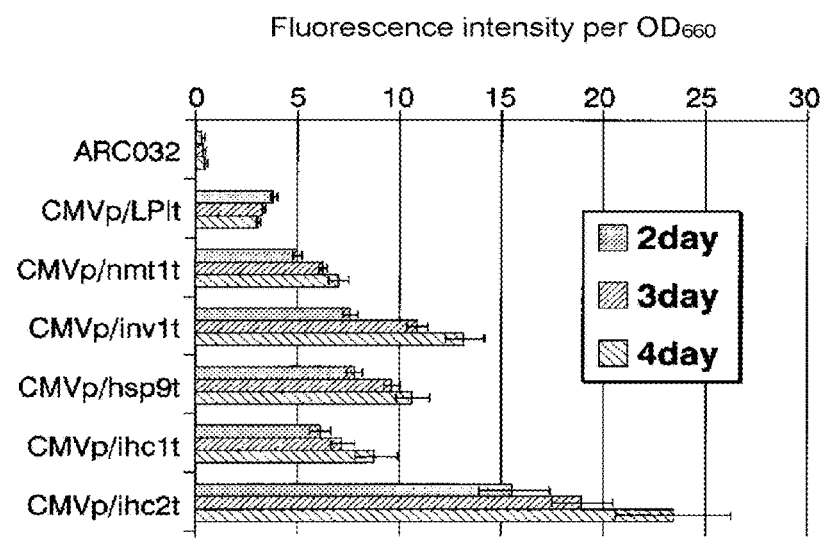
FIG. 1 is a graph illustrating results of calculation of GFP fluorescence intensity per $OD_{660}$ (GFP/$OD_{660}$) of each of transformants and ARC032 strain cultivated 2 to 4 days in Example 1.

The cloning vector of the present invention is a cloning vector for producing an expression vector to be introduced to a yeast of the genus *Schizosaccharomyces* for the expression of a protein derived from a foreign structural gene (hereinafter sometimes referred to as a foreign protein), and is characterized by having ihc2 gene terminator (hereinafter referred to as ihc2 terminator) of the yeast of the genus *Schizosaccharomyces* as a terminator which controls the expression of the foreign structural gene. The cloning vector of the present invention, which controls expression of a foreign structural protein by the ihc2 terminator, is capable of expressing a foreign protein using *S. pombe* as a host with a higher expression efficiency than in a case of using human lipocortin-I (hLPI) terminator, SV40 terminator, nmt1 terminator or the like which is commonly used for expressing a foreign protein.

The ihc2 terminator to be used for the cloning vector of the present invention may be a terminator derived from any yeast of the genus *Schizosaccharomyces* so long as it is ihc2 terminator gene of the yeast of the genus *Schizosaccharomyces*. As yeasts of the genus *Schizosaccharomyces*, *S. pombe*, *Schizosaccharomyces japonicus* and *Schizosaccharomyces octosporus* may, for example, be mentioned. The ihc2 terminator to be used for the cloning vector may be derived from the same biological species as the yeast of the genus *Schizosaccharomyces* to which an expression vector produced from the cloning vector is to be introduced, or may be derived from a different biological species. In the present invention, it is preferred to use the ihc2 terminator of *S. pombe*, which is more widely used.

The ihc2 gene of *S. pombe* is known, and the systematic name of ihc2 gene registered in a gene sequence database of *S. pombe* (Pam Base; http://www.pombase.org/) provided by European Bioinformatics Institute is The ihc2 terminator used for the cloning vector of the present invention may be a region which is composed of a nucleotide sequence identical to the terminator endogenous to a wild-type yeast of the genus *Schizosaccharomyces* (wild-type ihc2 terminator) and is further composed of the nucleotide sequence having deletion, substitution or addition of at least one nucleotide, preferably from one to tens nucleotides, more preferably from one to dozen nucleotides, further preferably from one to nine nucleotides, even further preferably from one to few nucleotides, and has a terminator activity similar to the wild-type ihc2 terminator. The terminator activity means a function as a terminator.

Further, the ihc2 terminator to be used for the cloning vector of the present invention may be a region which has a terminator activity similar to the wild-type ihc2 terminator and is composed of a nucleotide sequence having a homology to a nucleotide sequence identical to the wild-type ihc2 terminator of at least 80%, preferably at least 85%, more preferably at least 90%, further preferably at least 95%.

The ihc2 terminator of *S. pombe* is a region 1 to 625 bp downstream from the 3' end (the third nucleotide of the stop codon) of ihc2 gene ORF (SEQ ID NO:19). The nucleotide sequence of the region is shown as SEQ ID NO:19. That is, the cloning vector of the present invention preferably contains a region composed of a nucleotide sequence represented by SEQ ID NO:19. Further, a region which has a terminator activity similar to the wild-type ihc2 terminator and is composed of a nucleotide sequence represented by SEQ ID NO:19 having deletion, substitution or addition of at least one nucleotide, preferably from one to tens nucleotides, more preferably from one to dozen nucleotides, further preferably from one to nine nucleotides, even further preferably from one to few nucleotides, or a nucleotide sequence having a homology to a sequence represented by SEQ ID NO:19 of at least 80%, preferably at least 85%, more preferably at least 90%, further preferably at least 95%, may also be used suitably as the ihc2 terminator for the cloning vector of the present invention.

From the viewpoint of the expression efficiency, the ihc2 terminator of S. pombe preferably contains a region 1 to 525 bp downstream from the 3' end (the third nucleotide of the stop codon) of ihc2 gene ORF, more preferably 1 to 400 bp, further preferably 1 to 300 bp, particularly preferably 1 to 200 bp, most preferably 1 to 175 bp.

The cloning vector of the present invention has, in addition to the ihc2 terminator of the yeast of the genus Schizosaccharomyces, a promoter capable of functioning in the yeast of the genus Schizosaccharomyces, and a cloning site for introducing a foreign structural gene which is located downstream from the promoter and is regulated by the promoter.

As the promotor of the cloning vector of the present invention, a promoter endogenous to the yeast of the genus Schizosaccharomyces or a promoter exogenous to the yeast of the genus Schizosaccharomyces may be used. Further, two or more types of promotors may be present in the vector. As the promoter endogenous to the yeast of the genus Schizosaccharomyces, alcohol dehydrogenase (adh1) gene promoter, nmt1 gene promoter involved in thiamine metabolism, fructose-1,6-bis phosphatase (fbp1) gene promoter involved in glucose metabolism, invertase (inv1) gene promoter involved in catabolite repression (WO99/23223), heat shock protein gene promoter (WO2007/26617), inch1 gene (SPAC22G7.11c) promoter (WO2014/030644), and hsp9 gene (SPAP8A3.04c) promoter (WO2014/030644) may, for example, be mentioned.

As the promoter exogenous to the yeast of the genus Schizosaccharomyces, promoters derived from animal cell viruses disclosed in JP-A-5-15380, JP-A-7-163373 and JP-A-10-234375 may, for example, be mentioned, and hCMV promoter and SV40 promoter are preferred.

The cloning site contained in the cloning vector of the present invention is a restriction enzyme site which exists only in the cloning site of the cloning vector. The cloning site contained in the cloning vector of the present invention may have only one restriction enzyme site, or may be a multiple cloning site having at least two restriction enzyme sites. As the multiple cloning site, a multiple cloning site contained in publicly known cloning vectors can be used as it is, and one prepared by appropriately modifying a publicly known multiple cloning site can also be used. In addition, the cloning vector of the present invention may have an initiation codon (ATG) at an upstream end region inside the cloning site or at the upstream from the cloning site, and may have a stop codon at a downstream end region inside of the cloning site or at the downstream from the cloning site.

The cloning vector of the present invention preferably contains a 5'-untranslated region located downstream from the promoter and upstream from the cloning site, and preferably contains a 3'-untranslated region located downstream from the cloning site. Further, the cloning vector of the present invention preferably contains, at the cloning site, a marker for discriminating it from an expression vector having a foreign structural gene introduced therein. As the marker, a drug resistance gene capable of functioning in E. coli such as an ampicillin resistance gene may, for example, be mentioned. Further, the cloning vector of the present invention preferably contains a marker for selecting a transformant. As the marker, auxotrophic complementation markers such as orotidine 5'-phosphate decarboxylase (ura4 gene) and isopropyl malate dehydrogenase gene (leu1 gene) may, for example, be mentioned.

The cloning vector of the present invention is a vector having a circular DNA structure or a linear DNA structure. In the case of preparing a transformant in which the after-mentioned expression cassette is maintained as an extrachromosomal gene in cells of the yeast of the genus Schizosaccharomyces, the cloning vector of the present invention is preferably an expression vector which contains a sequence required for replication in the yeast of the genus Schizosaccharomyces, i.e. autonomously replicating sequence (ARS). On the other hand, in the case of preparing a transformant in which the after-mentioned expression cassette is integrated into chromosome of the yeast of the genus Schizosaccharomyces, the cloning vector of the present invention is preferably one having a linear DNA structure and having no ARS.

For example, in the case of preparing a transformant in which the after-mentioned expression cassette is integrated into chromosome of the yeast of the genus Schizosaccharomyces, the cloning vector of the present invention may be a vector comprising linear DNA or may be a vector having a circular DNA structure having a restriction enzyme site which cuts open to linear DNA at the time of introduction of the expression cassette into a host cell. In a case where the cloning vector of the present invention has an ARS, the ARS site may be eliminated to produce an expression cassette having a linear DNA structure, or the ARS site may be cut open to produce an expression cassette having a linear DNA structure having the ARS inactivated, and such an expression cassette is introduced into a host cell.

The cloning vector of the present invention can be produced by replacing a terminator region, which is contained in a publicly known cloning vector to be used for producing the expression vector for expressing a protein encoded by a foreign structural gene in a host, with ihc2 terminator of the yeast of the genus Schizosaccharomyces. As specific methods for constructing the cloning vector of the present invention, publicly known methods can be used. For example, an operation method described in the article [J. Sambrook et al., "Molecular Cloning 2nd ed.", Cold Spring Harbor Laboratory Press (1989)] may be used. In addition, the cloning vector may be constructed by an enzymatic amplification method using PCR, a chemical synthesis, or the like.

[Expression Vector and its Production Method]

The expression vector of the present invention comprises a promoter capable of functioning in the yeast of the genus Schizosaccharomyces, a foreign structural gene which is located downstream from the promoter and is regulated by the promoter, and ihc2 gene terminator of the yeast of the genus Schizosaccharomyces. The ihc2 terminator in the expression vector of the present invention is a terminator capable of controlling expression of a foreign structural gene in the expression vector and having the terminator activity described above for the cloning vector of the present invention.

Further, the expression vector of the present invention may have, in addition to the promoter, the foreign structural gene and the ihc2 terminator, the above-described 5'-untranslated region, 3'-untranslated region, auxotrophic complementation marker and the like.

A region containing the promoter, the foreign structural gene and the ihc2 terminator in the expression vector will hereinafter sometimes be referred to as an expression cassette. The expression cassette may have the above-described 5'-untranslated region, 3'-untranslated region, auxotrophic complementation marker and the like.

The foreign structural gene introduced into the expression vector of the present invention is not particularly limited so long as it is a structural gene encoding a protein, and may be a gene homologous to a gene endogenous to the yeast of the genus *Schizosaccharomyces* as a host or a structural gene derived from a heterologous organism. From a transformant of the yeast of the genus *Schizosaccharomyces* obtained by using an expression vector containing a structural gene encoding an endogenous protein of the yeast of the genus *Schizosaccharomyces*, a large amount of the endogenous protein can be produced. Further, from a transformant of the yeast of the genus *Schizosaccharomyces* obtained by using an expression vector containing a structural gene derived from a heterologous organism, a large amount of heterologous proteins (proteins exogenous to the host) can be produced.

The protein encoded by a foreign structural gene introduced into the expression vector of the present invention is preferably a heterologous protein, more preferably a protein produced by multicellular organisms such as animals and plants, especially a protein produced by a mammal (including humans). Such a protein is rarely obtained with high activity if a prokaryotic host microorganism such as *E. coli* is used for its production, and its production efficiency is generally low if an animal cell such as CHO cell is used as a host. These problems can be solved by using the expression vector of the present invention and employing a heterologous protein expression system in which a yeast of the genus *Schizosaccharomyces* is used as a host.

The foreign structural gene introduced into the expression vector of the present invention may be a wild-type structural gene, a gene prepared by modifying a wild-type structural gene, or an artificially synthesized gene, so long as it encodes a protein. As a non-wild-type structural gene, a gene encoding a chimeric protein in which two or more wild-type proteins are fused one another and a gene encoding a protein in which an additional peptide or the like is bound to the N-terminal or C-terminal of a wild-type protein may, for example, be mentioned. As the additional peptide, a signal such as a secretion signal, an organelle localization signal or the like, and a tag such as His-tag or FLAG-tag may, for example, be mentioned. The signal should be a signal which functions in a yeast of the genus *Schizosaccharomyces*. The secretion signal is a peptide introduced at the N-terminal and having a function of secreting the expressed protein out of the host cell. As the secretion signal which functions in a yeast of the genus *Schizosaccharomyces*, P3 signal described in WO1996/23890 is particularly preferred.

The expression vector of the present invention can be produced by introducing a foreign structural gene into a cloning site of the cloning vector of the present invention. The introduction of the foreign structural gene into the cloning site may be carried out by using publicly known methods, like the production of the cloning vector.

Further, the expression vector of the present invention may be produced without using the cloning vector of the present invention. For example, the expression vector of the present invention may be produced by introducing ihc2 terminator to an expression vector having no ihc2 terminator. Specifically, the expression vector of the present invention may be produced by replacing, of an expression vector having the above-described promoter, the foreign structural gene and a terminator other than the ihc2 terminator (hereinafter sometimes referred to as other terminator), said other terminator with ihc2 terminator. Otherwise, the expression vector of the present invention may be produced by introducing ihc2 terminator into an expression vector having the promoter and the foreign structural gene and having no terminator.

The expression vector having other terminator and the expression vector having no terminator may be produced by publicly known methods used for producing an expression vector for expressing a protein encoded by a foreign structural gene to a host. Further, exiting expression vectors (having other terminator or having no terminator) having various foreign structural genes may also be employed. Replacement with the terminator or introduction of the terminator in the expression vector may be carried out by publicly known methods used for producing an expression vector.

[Transformant and its Production Method]

The transformant of the present invention is characterized by having an expression cassette containing the promoter derived from the above-described expression vector of the present invention, the foreign structural gene and the ihc2 gene terminator. The expression cassette may have a 5'-untranslated region, a 3'-untranslated region, an auxotrophic complementation marker, etc., as described above.

A transformant having the expression cassette out of its chromosome maintains an expression vector containing the expression cassette out of the chromosome. The expression vector usually has a circular DNA structure having the ARS. On the other hand, a transformant having the expression cassette in its chromosome, has a chromosome containing an expression cassette having a linear DNA structure having no ARS.

The expression cassette having a linear DNA structure for introduction into the chromosome may be produced, for example, by cutting the expression vector of the present invention having a circular DNA structure having a restriction enzyme site for cutting open to linear DNA. Further, in a case where the expression vector of the present invention has an ARS, the ARS site is deleted or inactivated to produce linear DNA.

(Host)

The host for the transformant of the present invention is a yeast of the genus *Schizosaccharomyces*. The yeast of the genus *Schizosaccharomyces* used in the present invention may be a wild-type or a mutant-type in which a specific gene is deleted or inactivated depending on application. For deletion or inactivation of a specific gene, publicly known methods can be used. Specifically, the Latour system (Nucleic Acids Res. (2006) 34: e11, and WO2007/063919) can be used to delete the gene. Further, the gene can be inactivated by mutating the gene at a certain position by mutant screening using mutagens (Koubo Bunshi Idengaku Jikken-Hou, 1996, Japan Scientific Societies Press), random mutations using PCR (PCR Methods Appl., 1992, vol. 2, p. 28-33) and the like. As the yeast of the genus *Schizosaccharomyces* host in which a specific gene is deleted or inactivated, ones disclosed in WO2002/101038, WO2007/015470, etc. may be used.

Further, the host is preferably a yeast of the genus *Schizosaccharomyces* having a marker for selecting a transformant. For example, it is preferred to use a host which essentially requires a specific nutrient factor for growth due to deletion of a certain gene. When preparing a transformant by using a vector containing a target gene sequence, a transformant lacking the auxotrophy of the host can be obtained by using a vector carrying the deleted gene (auxotrophic complementation marker). It is possible to select the transformant by using the difference in auxotrophy between the host and the transformant.

For example, the yeast of the genus *Schizosaccharomyces* host, which has been made auxotrophic for uracil by deletion or inactivation of ura4 gene, is transformed with an expression vector containing ura4 gene, and transformants carrying the expression vector are obtained by selecting ones lacking uracil auxotrophy.

As the yeast of the genus *Schizosaccharomyces* host, one belonging to the above-mentioned species may be used. Among the above-described yeasts of the genus *Schizosaccharomyces*, *S. pombe* is preferred in view of the availability of various useful mutant strains. The *S. pombe* strain to be used in the present invention may, for example, be ATCC38399 (leu1-32, h⁻) or ATCC38436 (ura4-294, h⁻), which is available from the American Type Culture Collection.

(Transformation Method)

The yeast of the genus *Schizosaccharomyces* host is transformed by using the above-described expression vector. As the transformation method, any known transformation method for a yeast of the genus *Schizosaccharomyces* may be used. Such a transformation method may, for example, be a conventional method like a lithium acetate method [K. Okazaki et al., Nucleic Acids Res., 18, 6485-6489 (1990)], electroporation method, spheroplast method, glass-beads method, or the like, and a method disclosed in JP-A-2005-198612. Further, a commercially available yeast transformation kit may be used.

After transformation, the resulting transformants are usually subjected to selection. The selection may, for example, be carried out as follows. Screening is carried out by a culture broth which can select transformants by the above-mentioned auxotrophic marker, and two or more colonies are selected among the obtained colonies. In addition, the copy numbers of a vector and an expression cassette integrated into the chromosomes can be identified by subjecting the selected transformants to a genomic analysis using pulse-field gel electrophoresis.

(Cultivation Method)

The transformant of the present invention may be cultivated in the same manner as a natural yeast of the genus *Schizosaccharomyces*.

As the culture broth for cultivating the transformant of the present invention, a publicly known culture broth for yeasts may be used so long as it contains carbon sources, nitrogen sources, inorganic salts and the like which yeast of the genus *Schizosaccharomyces* can use, and yeast of the genus *Schizosaccharomyces* can grow in it efficiently. The culture broth may be natural or synthetic.

As the carbon sources, saccharides such as glucose, fructose and sucrose may, for example, be mentioned.

As the nitrogen sources, inorganic acids or inorganic ammonium salts such as ammonia, ammonium chloride and ammonium acetate, peptone and casamino acid may, for example, be mentioned.

As inorganic salts, magnesium phosphate, magnesium sulfate and sodium chloride may, for example, be mentioned.

Specifically, a nutrient medium such as YPD medium (M. D. Rose et al., "Methods In Yeast Genetics", Cold Spring Harbor Laboratory Press (1990)), a minimal medium such as MB Medium (K. Okazaki et al., Nucleic Acids Res., vol. 18, p. 6485-6489 (1990)) and the like may be used.

Publicly known yeast cultivation methods including a shaking cultivation and a stirring cultivation may, for example, be used.

Further, the cultivation temperature is preferably from 23 to 37° C. Further, the cultivation time may be set appropriately.

Cultivation may be carried out by batch culture or continuous culture.

[Method for Producing Protein]

The method for producing a protein of the present invention is characterized by cultivating a transformant containing an expression vector having a foreign structural gene introduced into a cloning site of the cloning vector described above, and, from cells or a culture supernatant thereby obtained, recovering a protein encoded by the above-described foreign structural gene.

The cultivation conditions can be set appropriately taking into consideration the type, etc. of a foreign protein of interest to be produced. For example, at a temperature of from 16 to 42° C., preferably from 25 to 37° C., and a cultivation time of from 8 to 168 hours, preferably from 48 to 96 hours. Either shaking culture or static culture can be employed, and stirring or aeration may be applied if necessary.

At the end of cultivation, cells are ruptured sonically or mechanically to obtain a cell extract containing the foreign protein of interest, whereby the foreign protein can be isolated and purified from the cell extract. Further, in a case where the foreign protein is secreted out of the cells, the foreign protein can be isolated and purified from the culture supernatant. As the isolation and purification method for recovering the produced protein, publicly known methods including a method utilizing difference in solubility such as salting out or solvent precipitation, a method utilizing difference in molecular weight such as dialysis, ultrafiltration or gel electrophoresis, a method utilizing difference in electric charge such as ion-exchange chromatography, a method utilizing specific affinity such as affinity chromatography, a method utilizing difference in hydrophobicity such as reverse phase high performance liquid chromatography, and a method utilizing difference in isoelectric point such as isoelectric focusing may, for example, be mentioned.

The isolated and purified protein can be identified by a publicly known method such as western blotting or an activity measurement method. The structure of the purified protein can be identified by amino acid analysis, amino-terminal analysis, primary structure analysis and the like.

EXAMPLES

Now, the present invention will be described in further detail with reference to Examples and Comparative Examples. However, it should be understood that the present invention is by no means thereby restricted.

Example 1

Using EGFP as a model protein, the difference in the EGFP expression amount by the type of the terminator derived from *S. pombe* was compared.

<Production of EGFP Expression Vector>

(pSL6EGFP-LPIt)

EGFP expression vector pSL6EGFP-LPIt having a structural gene encoding EGFP integrated into a multiple cloning site of publicly-known single-locus integration vector pSL6 (Alimjan et al., Appl Microbiol Biotechnol, 2010, vol.85, pp.667-677) was produced. The pSL6 vector is a single-locus integration vector having a multiple cloning site between hCMV promoter and LPI terminator, for integrating a foreign gene into leu1 gene locus of *S. pombe*.

Specifically, first, PCR was carried out by using an artificial gene encoding EGFP (SEQ ID NO: 1) as a template, a forward primer (SEQ ID NO: 2) comprising the restriction enzyme recognition site for NcoI at the 5' end, and a reverse primer (SEQ ID NO: 3) comprising the restriction enzyme recognition site for PstI at the 5' end, thereby to obtain a PCR product (EGFP fragment) having the restriction enzyme recognition site for NcoI at the 5' end and the restriction enzyme recognition site for PstI at the 3' end of the whole ORF of EGFP gene.

The EGFP fragment was subjected to double digestion with restriction enzymes NcoI and PstI, pSL6 was subjected to double digestion with restriction enzymes AarI and PstI, and both digested products were ligated to each other for transforming E. coli DH5a to obtain a plasmid. The obtained plasmid was named as EGFP expression vector pSL6EGFP-LPIt.

(pSL6EGFP-inv1t)

EGFP expression vector pSL6EGFP-inv1t having LPI terminator in the above-produced pSL6EGFP-LPIt vector replaced with inv1 terminator in publicly-known single-locus integration vector pSL9 (WO2014/030644) was produced. The pSL9 vector is a single-locus integration vector having a multiple cloning site between inv1 promoter derived from S. pombe and inv1 terminator (a region 1 bp to 548 bp downstream from the inv1 gene (SPCC191.11) ORF, SEQ ID NO:4), for integrating a foreign gene into the leu1 gene locus of S. pombe.

Specifically, pSL6EGFP-LPIt was subjected to double digestion with restriction enzymes PstI and EcoRI to remove LPI terminator portion, and pSL9 was subjected to double digestion with restriction enzymes PstI and EcoRI to recover inv1 terminator portion, and both digested products were ligated to each other for transforming E. coli DH5α to obtain a plasmid. The obtained plasmid was named as EGFP expression vector pSL6EGFP-inv1t.

(pSL6EGFP-nmt1t)

EGFP expression vector pSL6EGFP-nmt1t having LPI terminator of pSL6EGFP-LPIt vector replaced with nmt1 terminator derived from S. pombe, was produced.

Specifically, PCR was carried out by using a genomic DNA derived from a wild-type strain (ARC032 strain, corresponding to ATCC38366, 972h⁻) of S. pombe as a template, a forward primer (SEQ ID NO: 5) comprising the restriction enzyme recognition site for PstI at the 5' end, and a reverse primer (SEQ ID NO: 6) comprising the restriction enzyme recognition site for EcoRI at the 5' end, thereby to obtain a PCR product (nmt1t fragment) having the restriction enzyme recognition site for PstI at the 5' end and the restriction enzyme recognition site for EcoRI at the 3' end of a region (SEQ ID NO:7) 1 bp to 573 bp downstream from nmt1 gene (SPCC1223.02) ORF.

The nmt1t fragment was subjected to double digestion with restriction enzymes PstI and EcoRI, and pSL6EGFP-LPIt was subjected to double digestion with restriction enzymes PstI and EcoRI to remove LPI terminator portion, and both digested products were ligated to each other for transforming E. coli DH5α to obtain a plasmid. The obtained plasmid was named as EGFP expression vector pSL6EGFP-nmt1t.

(pSL6EGFP-hsp9t)

EGFP expression vector pSL6EGFP-hsp9t having LPI terminator of pSL6EGFP-LPIt vector replaced with hsp9 terminator derived from S. pombe, was produced.

Specifically, PCR was carried out by using a genomic DNA derived from a wild-type strain (ARC032 strain) of S. pombe as a template, a forward primer (SEQ ID NO: 8) comprising the restriction enzyme recognition site for PstI at the 5' end, and a reverse primer (SEQ ID NO: 9) comprising the restriction enzyme recognition site for SpeI at the 5' end, thereby to obtain a PCR product (hsp9t fragment) having the restriction enzyme recognition site for PstI at the 5' end and the restriction enzyme recognition site for SpeI at the 3' end of a region (SEQ ID NO:10) 1 bp to 545 bp downstream from hsp9 gene (SPAP8A3.04C) ORF.

The hsp9t fragment was subjected to double digestion with restriction enzymes PstI and SpeI, and pSL6EGFP-LPIt was subjected to double digestion with restriction enzymes PstI and SpeI to remove LPI terminator portion, and both digested products were ligated to each other for transforming E. coli DH5α to obtain a plasmid. The obtained plasmid was named as EGFP expression vector pSL6EGFP-hsp9t.

(pSL6EGFP-hsp16t)

EGFP expression vector pSL6EGFP-hsp16t having LPI terminator of pSL6EGFP-LPIt vector replaced with hsp16 terminator derived from S. pombe, was produced.

Specifically, PCR was carried out by using a genomic DNA derived from a wild-type strain (ARC032 strain) of S. pombe as a template, a forward primer (SEQ ID NO: 11) comprising the restriction enzyme recognition site for PstI at the 5' end, and a reverse primer (SEQ ID NO: 12) comprising the restriction enzyme recognition site for EcoRI at the 5' end, thereby to obtain a PCR product (hsp16t fragment) having the restriction enzyme recognition site for PstI at the 5' end and the restriction enzyme recognition site for EcoRI at the 3' end of a region (SEQ ID NO:13) 1 bp to 527 bp downstream from hsp16 gene (SPBC3E7.02c) ORF.

The hsp16t fragment was subjected to double digestion with restriction enzymes PstI and EcoRI, and pSL6EGFP-LPIt was subjected to double digestion with restriction enzymes PstI and EcoRI to remove LPI terminator portion, and both digested products were ligated to each other for transforming E. coli DH5α to obtain a plasmid. The obtained plasmid was named as EGFP expression vector pSL6EGFP-hsp16t.

(pSL6EGFP-inch1t)

EGFP expression vector pSL6EGFP-inch1t having LPI terminator of pSL6EGFP-LPIt vector replaced with inch1 terminator derived from S. pombe, was produced.

Specifically, PCR was carried out by using a genomic DNA derived from a wild-type strain (ARC032 strain) of S. pombe as a template, a forward primer (SEQ ID NO: 14) comprising the restriction enzyme recognition site for PstI at the 5' end, and a reverse primer (SEQ ID NO: 15) comprising the restriction enzyme recognition site for SpeI at the 5' end, thereby to obtain a PCR product (ihc1t fragment) having the restriction enzyme recognition site for PstI at the 5' end and the restriction enzyme recognition site for SpeI at the 3' end of a region (SEQ ID NO:16) 1 bp to 520 bp downstream from inch1 gene (SPAC22G7.11c) ORF.

The ihc1t fragment was subjected to double digestion with restriction enzymes PstI and SpeI, and pSL6EGFP-LPIt was subjected to double digestion with restriction enzymes PstI and SpeI to remove LPI terminator portion, and both digested products were ligated to each other for transforming E. coli DH5α to obtain a plasmid. The obtained plasmid was named as EGFP expression vector pSL6EGFP-inch1t.

(pSL6EGFP-ihc2t)

EGFP expression vector pSL6EGFP-ihc2t having LPI terminator of pSL6EGFP-LPIt vector replaced with ihc2 terminator derived from S. pombe, was produced.

Specifically, PCR was carried out by using a genomic DNA derived from a wild-type strain (ARC032 strain) of S. pombe as a template, a forward primer (SEQ ID NO: 17)

comprising the restriction enzyme recognition site for PstI at the 5' end, and a reverse primer (SEQ ID NO: 18) comprising the restriction enzyme recognition site for EcoRI at the 5' end, thereby to obtain a PCR product (ihc2t fragment) having the restriction enzyme recognition site for PstI at the 5' end and the restriction enzyme recognition site for EcoRI at the 3' end of a region (SEQ ID NO:19) 1 bp to 625 bp downstream from ihc2 gene (SPAC11D3.01c) ORF.

The ihc2t fragment was subjected to double digestion with restriction enzymes PstI and EcoRI, and pSL6EGFP-LPIt was subjected to double digestion with restriction enzymes PstI and EcoRI to remove LPI terminator portion, and both digested products were ligated to each other for transforming E. coli DH5α to obtain a plasmid. The obtained plasmid was named as EGFP expression vector pSL6EGFP-ihc2t.

(pSL6EGFP-adh1t)

EGFP expression vector pSL6EGFP-adh1t having LPI terminator of pSL6EGFP-LPIt vector replaced with adh1 terminator derived from S. pombe, was produced.

Specifically, PCR was carried out by using a genomic DNA derived from a wild-type strain (ARC032 strain) of S. pombe as a template, a forward primer (SEQ ID NO: 20) comprising the restriction enzyme recognition site for PstI at the 5' end, and a reverse primer (SEQ ID NO: 21) comprising the restriction enzyme recognition site for EcoRI at the 5' end, thereby to obtain a PCR product (adh1t fragment) having the restriction enzyme recognition site for PstI at the 5' end and the restriction enzyme recognition site for EcoRI at the 3' end of a region (SEQ ID NO:22) 1 bp to 528 bp downstream from adh1 gene (SPCC13B11.01) ORF.

The adh1t fragment was subjected to double digestion with restriction enzymes PstI and EcoRI, and pSL6EGFP-LPIt was subjected to double digestion with restriction enzymes PstI and EcoRI to remove LPI terminator portion, and both digested products were ligated to each other for transforming E. coli DH5α to obtain a plasmid. The obtained plasmid was named as EGFP expression vector pSL6EGFP-adh1t.

(pSL6EGFP-act1t)

EGFP expression vector pSL6EGFP-act1t having LPI terminator of pSL6EGFP-LPIt vector replaced with act1 terminator derived from S. pombe, was produced.

Specifically, PCR was carried out by using a genomic DNA derived from a wild-type strain (ARC032 strain) of S. pombe as a template, a forward primer (SEQ ID NO: 23) comprising the restriction enzyme recognition site for PstI at the 5' end, and a reverse primer (SEQ ID NO: 24) comprising the restriction enzyme recognition site for EcoRI at the 5' end, thereby to obtain a PCR product (act1t fragment) having the restriction enzyme recognition site for PstI at the 5' end and the restriction enzyme recognition site for EcoRI at the 3' end of a region (SEQ ID NO:25) 1 bp to 783 bp downstream from act1 gene (SPBC32H8.12c) ORF.

The act1t fragment was subjected to double digestion with restriction enzymes PstI and EcoRI, and pSL6EGFP-LPIt was subjected to double digestion with restriction enzymes PstI and EcoRI to remove LPI terminator portion, and both digested products were ligated to each other for transforming E. coli DH5α to obtain a plasmid. The obtained plasmid was named as EGFP expression vector pSL6EGFP-act1t.

(pSL6EGFP-bip1t)

EGFP expression vector pSL6EGFP-bip1t having LPI terminator of pSL6EGFP-LPIt vector replaced with ura4 terminator derived from S. pombe, was produced.

Specifically, PCR was carried out by using a genomic DNA derived from a wild-type strain (ARC032 strain) of S. pombe as a template, a forward primer (SEQ ID NO: 26) comprising the restriction enzyme recognition site for PstI at the 5' end, and a reverse primer (SEQ ID NO: 27) comprising the restriction enzyme recognition site for EcoRI at the 5' end, thereby to obtain a PCR product (bip1t fragment) having the restriction enzyme recognition site for PstI at the 5' end and the restriction enzyme recognition site for EcoRI at the 3' end of a region (SEQ ID NO:28) 1 bp to 719 bp downstream from bip1 gene (SPAC22A12.15c) ORF.

The bip1t fragment was subjected to double digestion with restriction enzymes PstI and EcoRI, and pSL6EGFP-LPIt was subjected to double digestion with restriction enzymes PstI and EcoRI to remove LPI terminator portion, and both digested products were ligated to each other for transforming E. coli DH5α to obtain a plasmid. The obtained plasmid was named as EGFP expression vector pSL6EGFP-bip1t.

(pSL6EGFP-ura4t)

EGFP expression vector pSL6EGFP-ura4t having LPI terminator of pSL6EGFP-LPIt vector replaced with bip1 terminator derived from S. pombe, was produced.

Specifically, PCR was carried out by using a genomic DNA derived from a wild-type strain (ARC032 strain) of S. pombe as a template, a forward primer (SEQ ID NO: 29) comprising the restriction enzyme recognition site for PstI at the 5' end, and a reverse primer (SEQ ID NO: 30) comprising the restriction enzyme recognition site for EcoRI at the 5' end, thereby to obtain a PCR product (ura4t fragment) having the restriction enzyme recognition site for PstI at the 5' end and the restriction enzyme recognition site for EcoRI at the 3' end of a region (SEQ ID NO:31) 1 bp to 529 bp downstream from ura4 gene (SPCC330.05c) ORF.

The ura4t fragment was subjected to double digestion with restriction enzymes PstI and EcoRI, and pSL6EGFP-LPIt was subjected to double digestion with restriction enzymes PstI and EcoRI to remove LPI terminator portion, and both digested products were ligated to each other for transforming E. coli DH5α to obtain a plasmid. The obtained plasmid was named as EGFP expression vector pSL6EGFP-ura4t.

(pSL6EGFP-leu1t)

EGFP expression vector pSL6EGFP-leu1t having LPI terminator of pSL6EGFP-LPIt vector replaced with leu1 terminator derived from S. pombe, was produced.

Specifically, PCR was carried out by using a genomic DNA derived from a wild-type strain (ARC032 strain) of S. pombe as a template, a forward primer (SEQ ID NO: 32) comprising the restriction enzyme recognition site for PstI at the 5' end, and a reverse primer (SEQ ID NO: 33) comprising the restriction enzyme recognition site for EcoRI at the 5' end, thereby to obtain a PCR product (leu1t fragment) having the restriction enzyme recognition site for PstI at the 5' end and the restriction enzyme recognition site for EcoRI at the 3' end of a region (SEQ ID NO:34) 1 bp to 516 bp downstream from leu1 gene (SPBC1A4.02c) ORF.

The leu1t fragment was subjected to double digestion with restriction enzymes PstI and EcoRI, and pSL6EGFP-LPIt was subjected to double digestion with restriction enzymes PstI and EcoRI to remove LPI terminator portion, and both digested products were ligated to each other for transforming E. coli DH5α to obtain a plasmid. The obtained plasmid was named as EGFP expression vector pSL6EGFP-leu1t.

(pSL6EGFP-ade6t)

EGFP expression vector pSL6EGFP-ade6t having LPI terminator of pSL6EGFP-LPIt vector replaced with ade6 terminator derived from S. pombe, was produced.

Specifically, PCR was carried out by using a genomic DNA derived from a wild-type strain (ARC032 strain) of *S. pombe* as a template, a forward primer (SEQ ID NO: 35) comprising the restriction enzyme recognition site for PstI at the 5' end, and a reverse primer (SEQ ID NO: 36) comprising the restriction enzyme recognition site for EcoRI, thereby to obtain a PCR product (ade6t fragment) having the restriction enzyme recognition site for PstI at the 5' end and the restriction enzyme recognition site for EcoRI at the 3' end of a region (SEQ ID NO:37) 1 bp to 416 bp downstream from ade6 gene (SPCC1322.13) ORF.

The ade6t fragment was subjected to double digestion with restriction enzymes PstI and EcoRI, and pSL6EGFP-LPIt was subjected to double digestion with restriction enzymes PstI and EcoRI to remove LPI terminator portion, and both digested products were ligated to each other for transforming *E. coli* DH5α to obtain a plasmid. The obtained plasmid was named as EGFP expression vector pSL6EGFP-ade6t.

(pSL6EGFP-ptr3t)

EGFP expression vector pSL6EGFP-ptr3t having LPI terminator of pSL6EGFP-LPIt vector replaced with ptr3 terminator derived from *S. pombe*, was produced.

Specifically, PCR was carried out by using a genomic DNA derived from a wild-type strain (ARC032 strain) of *S. pombe* as a template, a forward primer (SEQ ID NO: 38) comprising the restriction enzyme recognition site for PstI at the 5' end, and a reverse primer (SEQ ID NO: 39) comprising the restriction enzyme recognition site for EcoRI at the 5' end, thereby to obtain a PCR product (ptr3t fragment) having the restriction enzyme recognition site for PstI at the 5' end and the restriction enzyme recognition site for EcoRI at the 3' end of a region (SEQ ID NO:40) 1 bp to 538 bp downstream from ptr3 gene (SPBC1604.21c) ORF.

The ptr3t fragment was subjected to double digestion with restriction enzymes PstI and EcoRI, and pSL6EGFP-LPIt was subjected to double digestion with restriction enzymes PstI and EcoRI to remove LPI terminator portion, and both digested products were ligated to each other for transforming *E. coli* DH5α to obtain a plasmid. The obtained plasmid was named as EGFP expression vector pSL6EGFP-ptr3t.

<Host>

As the host, a leucine-auxotrophic strain (ARC001 strain, genotype: h⁻, leu1-32) of *S. pombe* was used.

<Production of Transformant>

The ARC001 strain was cultivated in YES medium (0.5% of yeast extract, 3% of glucose and 0.25 mg/ml of SP supplements) until 1.0 to $2.0 \times 10^7$ cells/ml. The cultivated cells were collected and washed, and then suspended in 0.1 M lithium acetate (pH 5.0) to $2.0 \times 10^9$ cells/ml. Thereafter, to 100 µl of the ARC001 strain suspension, about 1 µg of each of the above-obtained EGFP expression vectors pSL6EGFP-LPIt, pSL6EGFP-nmt1t, pSL6EGFP-inv1t, pSL6EGFP-hsp9t, pSL6EGFP-hsp16t, pSL6EGFP-ihc1t, pSL6EGFP-ihc2t, pSL6EGFP-adh1t, pSL6EGFP-act1t, pSL6EGFP-bip1t, pSL6EGFP-ura4t, pSL6EGFP-leu1 t, pSL6EGFP-ade6t and pSL6EGFP-ptr3t digested with restriction enzyme NotI, was added, and then 260 µl of a 50% (w/v) polyethylene glycol (PEG4000) aqueous solution was added thereto, followed by stirring and by incubation at 32° C. for 30 minutes, and 43 µl DMSO was added, followed by incubation at 42° C. for 5 minutes. PEG4000 was removed by centrifugation and then the cells were washed and suspended in 150 µl of sterile water, and the suspension was applied on a minimal agarose medium. The cells on the medium were cultivated for 3 to 5 days to obtain a transformant.

The transformants obtained by using the EGFP expression vectors pSL6EGFP-LPIt, pSL6EGFP-nmt1t, pSL6EGFP-inv1t, pSL6EGFP-hsp9t, pSL6EGFP-hsp16t, pSL6EGFP-ihc1t, pSL6EGFP-ihc2t, pSL6EGFP-adh1t, pSL6EGFP-act1t, pSL6EGFP-bip1t, pSL6EGFP-ura4t, pSL6EGFP-leu1t, pSL6EGFP-ade6t and pSL6EGFP-ptr3t were named respectively as CMVp/LPIt strain, CMVp/nmt1t strain, CMVp/inv1t strain, CMVp/hsp9t strain, CMVp/hsp16t strain, CMVp/inch1t strain, CMVp/ihc2t strain, CMVp/adh1t strain, CMVp/act1t strain, CMVp/bip1t strain, CMVp/ura4t strain, CMVp/leu1t strain, CMVp/ade6t strain and CMVp/ptr3t strain.

<Measurement of GFP Fluorescence Intensity of Cultivated Cell>

Each of the above-obtained transformants and a wild-type strain (ARC032 strain) of *S. pombe* which is a non-EGFP producing strain was inoculated in 5 mL of EMM medium (manufactured by MP BIOMEDICALS, USA) in a test tube and cultivated at 32° C. for 4 days. The cell-density ($OD_{660}$) and the GFP fluorescence intensity (excitation wavelength: 490 nm, fluorescence wavelength: 530 nm) of each culture broth 2 to 4 days after cultivation were measured by MTP-810Lab (manufactured by CORONA ELECTRIC Co., Ltd., Japan) to calculate the GFP fluorescence intensity per $OD_{660}$ ($GFP/OD_{660}$, reflecting the EGFP production per cell) of each of the transformants and ARC032 strain.

Every transformant showed GFP fluorescence after cultivating 2 days, indicating that each transformant produces EGFP. The results of calculation of $GFP/OD_{660}$ of each of ARC032 strain, CMVp/LPIt strain, CMVp/nmt1t strain, CMVp/inv1t strain, CMVp/hsp9t strain, CMVp/ihc1t strain and CMVp/ihc2t strain, at each cultivation time, are shown in FIG. 1.

Each of CMVp/nmt1t strain, CMVp/inv1t strain, CMVp/hsp9t strain, CMVp/ihc1t strain and CMVp/ihc2t strain showed a $GFP/OD_{660}$ value higher than that of CMVp/LPIt strain after cultivating 2 days, indicating that the production of EGFP improves. Among them, CMVp/ihc2t strain showed a particularly high $GFP/OD_{660}$ value, which was about 4 to 5 times that of CMVp/LPIt strain. Since $GFP/OD_{660}$ is considered to be substantially proportional to the EGFP production in the cell, it is indicated that the production of EGFP may be improved at least 4 times by changing the terminator which is located downstream from the EGFP gene in the EGFP expression cassette, from the LPI terminator to the ihc2 terminator. Further, CMVp/ihc2t strain even showed a $GFP/OD_{660}$ value higher than those of CMVp/nmt1t strain and CMVp/inv1t strain, using a terminator which has been used for *S. pombe* expression system, indicating that the production of a foreign gene may be improved by using ihc2 terminator instead of a conventional publicly-known terminator. Although it is not shown in data, CMVp/hsp16t strain, CMVp/adh1t strain, CMVp/act1t strain, CMVp/bip1t strain, CMVp/ura4t strain, CMVp/leu1t strain, CMVp/ade6t strain and CMVp/ptr3t strain showed $GFP/OD_{660}$ values equal to those of CMVp/nmt1t strain and CMVp/hsp9t strain. That is, CMVp/LPIt strain showed the lowest $GFP/OD_{660}$ value among the produced EGFP-producing strains. Only the LPI terminator is a sequence derived from human among the terminators used, and it is possible that the LPI terminator sequence may hardly function normally in *S. pombe* cells.

Example 2

Using YES medium and YPD medium which are frequently used for cultivation of *S. pombe*, influences of media over gene expression were observed.

<Measurement of GFP Fluorescence Intensity of Cells Cultivated in Each Medium>

Each of the transformants CMVp/LPIt strain, CMVp/nmt1t strain, CMVp/inv1t strain and CMVp/ihc2t strain, obtained in Example 1, and a wild-type strain of S. pombe (ARC032 strain) was inoculated in 5mL of EMM medium, YES medium or YPD medium (1% of yeast extract, 1% of peptone and 2% of glucose) in a test tube and cultivated at 32° C. for 3 days. The cell-density ($OD_{660}$) and the GFP fluorescence intensity (excitation wavelength: 490 nm, fluorescence wavelength: 530 nm) of each culture broth after cultivation were measured by MTP-810Lab to calculate the GFP fluorescence intensity per $OD_{660}$ (GFP/$OD_{660}$) of each of the transformants and the ARC032 strain.

Figure 2:
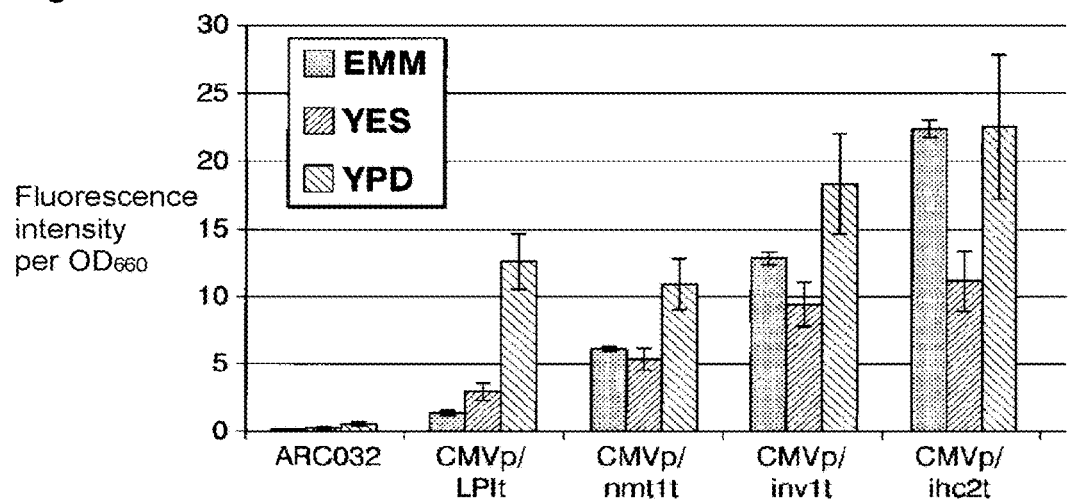
FIG. 2 is a graph illustrating results of calculation of GFP fluorescence intensity per $OD_{660}$ (GFP/$OD_{660}$) of each of transformants and ARC032 strain cultivated in EMM medium, YES medium and YPD medium in Example 1.

The results of calculation of GFP/$OD_{660}$ of each of ARC032 strain, CMVp/LPIt strain, CMVp/nmt1t strain, CMVp/inv1t strain and CMVp/ihc2t strain cultivated in each medium are shown in FIG. 2.

In cultivation in the EMM medium, in the same manner as in Example 1, CMVp/ihc2t strain showed the highest GFP/$OD_{660}$ value, which was at least 5 times that of CMVp/LPIt strain. In cultivation in the YPD medium, although every transformant showed a high GFP/$OD_{660}$ value, CMVp/ihc2t strain still showed a relatively high GFP/$OD_{660}$ value, and in cultivation in the YES medium also, CMVp/ihc2t strain showed a GFP/$OD_{660}$ value higher than those of CMVp/LPIt strain and CMVp/nmt1t strain. The effect to improve the EGFP production by using the ihc2 terminator in the YES medium or the YPD medium was sufficiently high although not so remarkable as observed in the EMM medium, suggesting that the effect to improve the expression efficiency by using the ihc2 terminator can be achieved regardless of the medium.

Example 3

Using inch1 promoter and hsp9 promoter which are derived from S. pombe, influences of the intensity of the promoter over gene expression were examined.

<Production of Vector pSL12inv1 t for Gene Locus Integration> leu1 gene locus integration vector pSL12inv1t (5998bp, SEQ ID NO: 41) having LPI terminator in publicly-known single-locus integration vector pSL12 (WO2014/030644) replaced with inv1 terminator, was produced. The pSL12 vector is a single-locus integration vector comprising a multiple cloning site between inch1 promoter and LPI terminator, for integrating a foreign gene into leu1 gene locus of S. pombe.

Figure 3:
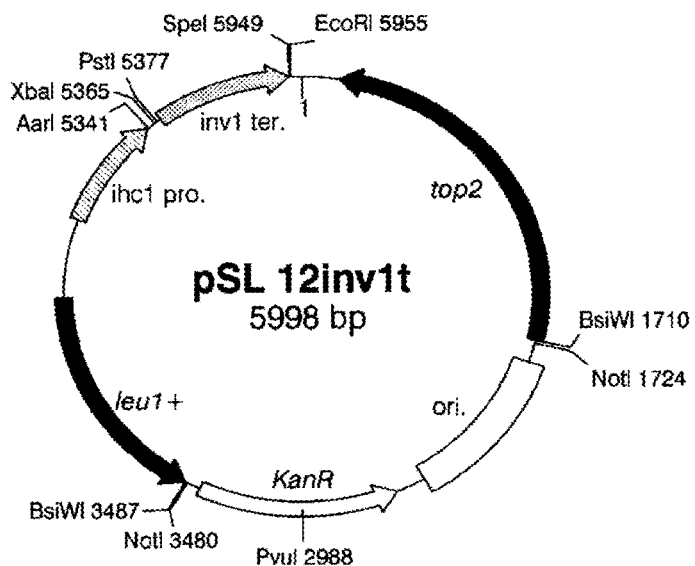
FIG. 3 is a diagram illustrating the structure of pSL12inv1t vector.

Specifically, pSL12 was subjected to double digestion with restriction enzymes PstI and SpeI to remove LPI terminator portion, and pSL6EGFP-inv1t constructed in Example 1 was subjected to double digestion with restriction enzymes PstI and SpeI to recover inv1 terminator portion, and both digested products were ligated to each other for transforming E. coli DH5α to obtain a plasmid. The obtained plasmid was named as pSL12inv1t. The structure of pSL12inv1t vector is shown in FIG. 3.

<Production of Gene Locus Integration Vector pSL12ihc2t> leu1 gene locus integration vector pSL12ihc2t (6057bp, SEQ ID NO: 42) having LPI terminator in single-locus integration vector pSL12 replaced with ihc2 terminator, was produced.

Specifically, PCR was carried out by using genomic DNA derived from a wild-type strain (ARC032 strain) of S. pombe as a template, a forward primer (SEQ ID NO: 17) comprising the restriction enzyme recognition site for PstI at the 5' end, and a reverse primer (SEQ ID NO: 43) comprising the restriction enzyme recognition site for SpeI at the 5' end, thereby to obtain a PCR product (ihc2t-Spe fragment) having the restriction enzyme recognition site for PstI at the 5' end and the restriction enzyme recognition site for SpeI at the 3' end of a region 1 bp to 625 bp downstream from ihc2 gene ORF.

Figure 4:
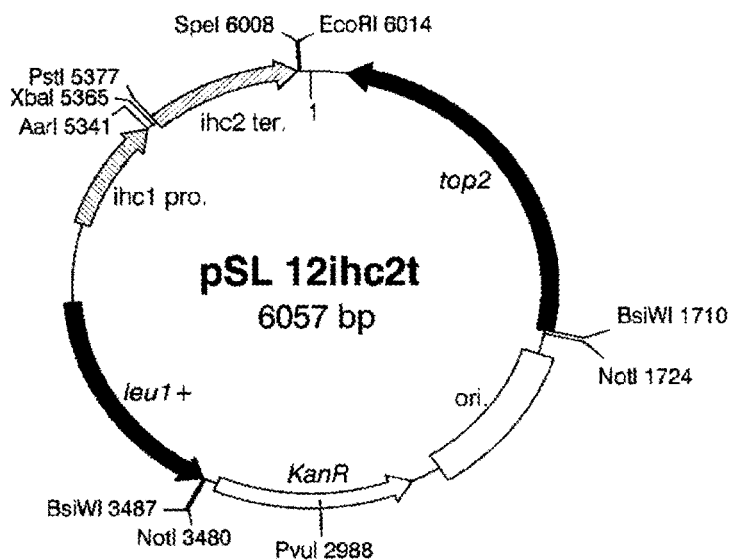
FIG. 4 is a diagram illustrating the structure of pSL12ihc2t vector.

The ihc2t-Spe fragment was subjected to double digestion with restriction enzymes PstI and SpeI, pSL12 was subjected to double digestion with restriction enzymes PstI and SpeI to remove LPI terminator portion, and both digested products were ligated to each other for transforming E. coli DH5α to obtain a plasmid. The obtained plasmid was named as pSL12ihc2t. The structure of pSL12ihc2t vector is shown in FIG. 4.

<Production of Gene Locus Integration Vector pSL14LPIt> leu1 gene locus integration vector pSL14LPIt (5778bp, SEQ ID NO: 44) having inv1 terminator in publicly-known single-locus integration vector pSL14lacZ (WO2014/030644) replaced with LPI terminator and having a structural gene encoding lacZ' removed, was produced. The pSL14lacZ vector is a single-locus integration vector comprising a structural gene encoding lacZ' and a multiple cloning site between hsp9 promoter and inv1 terminator, for integrating a foreign gene into leu1 gene locus of S. pombe.

Figure 5:
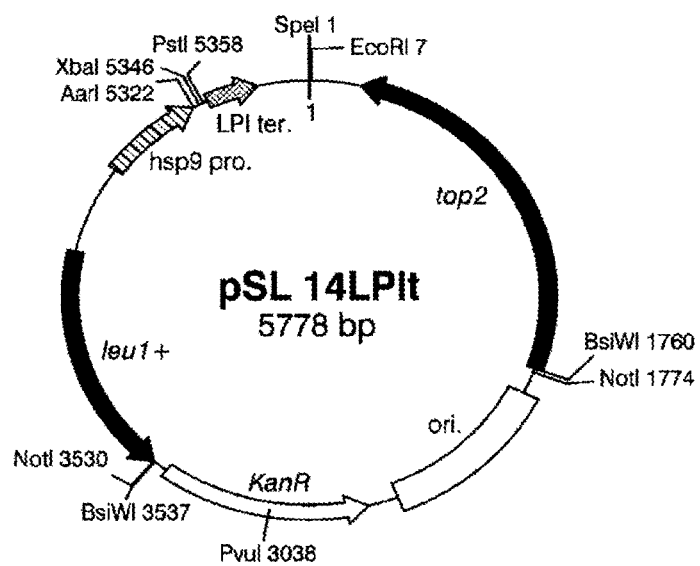
FIG. 5 is a diagram illustrating the structure of pSL14LPIt vector.

Specifically, pSL14lacZ was subjected to double digestion with restriction enzymes AarI and PvuI to recover a DNA fragment containing hsp9 promoter and a leu1 homologous recombination region, and pSL6 was subjected to double digestion with restriction enzymes AarI and PvuI to recover a DNA fragment containing LPI terminator and a top2 homologous recombination region, and both digested products were ligated to each other for transforming E. coli DH5α to obtain a plasmid. The obtained plasmid was named as pSL14LPIt. The structure of pSL14LPIt vector is shown in FIG. 5.

<Production of Gene Locus Integration Vector pSL14ihc2t> leu1 gene locus integration vector pSL14ihc2t vector (5988bp, SEQ ID NO: 45) having LPI terminator in single-locus integration vector pSL14LPIt replaced with ihc2 terminator, was produced.

Figure 6:
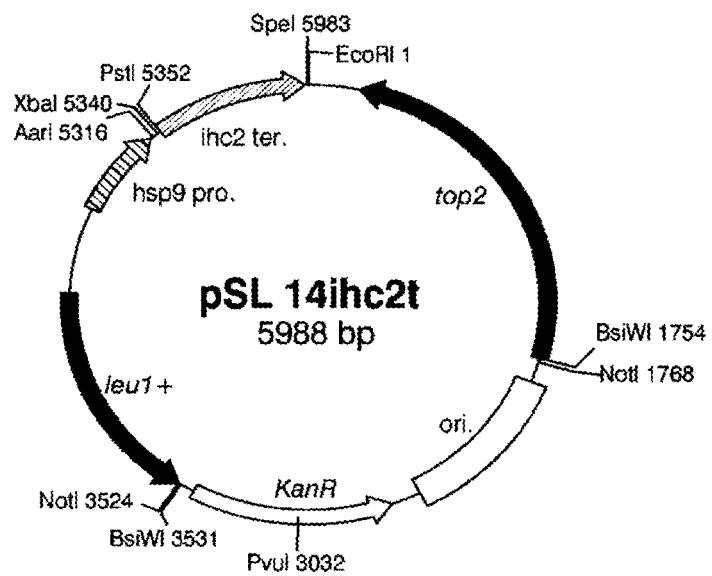
FIG. 6 is a diagram illustrating the structure of pSL14ihc2t vector.

Specifically, the above produced ihc2t-Spe fragment was subjected to double digestion with restriction enzymes PstI and SpeI, and the above constructed pSL14LPIt was subjected to double digestion with restriction enzymes PstI and SpeI to remove LPI terminator portion, and both digested products were ligated to each other for transforming E. coli DH5α to obtain a plasmid. The obtained plasmid was named as pSL14ihc2t. The structure of pSL14ihc2t vector is shown in FIG. 6.

<Production of EGFP Expression Vector>

(pSL12EGFP-LPIt, pSL12EGFP-inv1t, pSL12EGFP-ihc2t, pSL14EGFP-LPIt, pSL14EGFP-inv1t, pSL14EGFP-ihc2t)

EGFP expression vectors pSL12EGFP-inv1t, pSL12EGFP-ihc2t, pSL14EGFP-LPIt, pSL14EGFP-ihc2t, pSL12EGFP-LPIt and pSL14EGFP-inv1t, having a structural gene encoding EGFP integrated into the multiple cloning site of each of the above produced single-locus integration vectors pSL12inv1t, pSL12ihc2t, pSL14LPI1t and pSL14ihc2t and publicly-known single-locus integration vectors pSL12 and pSL14lacZ, were produced.

Specifically, the EGFP fragment produced in Example 1 was subjected to double digestion with restriction enzymes NcoI and PstI, and pSL12, pSL12inv1t, pSL12ihc2t, pSL14LPI1t, pSL14lacZ and pSL14ihc2t were subjected to double digestion with restriction enzymes AarI and PstI. The double-digested EGFP fragment and each of the double-digested single-locus integration vectors were ligated to each other for transforming *E. coli* DH5α to obtain a plasmid. The obtained plasmids were named as EGFP expression vectors pSL12EGFP-LPIt, pSL12EGFP-inv1t, pSL12EGFP-ihc2t, pSL14EGFP-LPIt, pSL14EGFP-inv1t and pSL14EGFP-ihc2t, respectively.

<Production of Transformant>

Using each of the produced expression vectors, in the same manner as in Example 1, transformants using ARC001 strain as a host were produced.

Transformants obtained by using EGFP expression vectors pSL12EGFP-LPIt, pSL12EGFP-inv1t, pSL12EGFP-ihc2t, pSL14EGFP-LPIt, pSL14EGFP-inv1t and pSL14EGFP-ihc2t were named as ihc1p/LPIt strain, ihc1p/inv1t strain, ihc1p/ihc2t strain, hsp9p/LPIt strain, hsp9p/inv1t strain and hsp9p/ihc2t strain, respectively.

<Measurement of GFP Fluorescence Intensity of Cultivated Cell>

Each of the transformants CMVp/LPIt strain, CMVp/inv1t strain and CMVp/ihc2t strain obtained in Example 1, the above obtained transformants, and a wild-type strain (ARC032 strain) of *S. pombe* was inoculated in 5mL of EMM medium in a test tube and cultivated at 32° C. for 3 days. The cell-density ($OD_{660}$) and the GFP fluorescence intensity (excitation wavelength: 490 nm, fluorescence wavelength: 530 nm) of each culture broth after cultivation were measured by MTP-810Lab to calculated the GFP fluorescence intensity per $OD_{660}$ ($GFP/OD_{660}$) of each of the transformants and the ARC032 strain.

Figure 7:
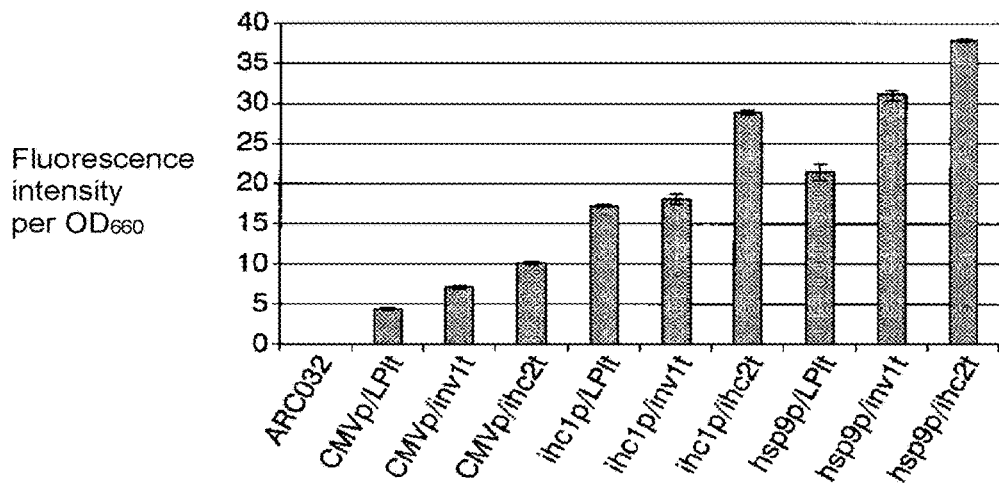
FIG. 7 is a graph illustrating results of calculation of GFP fluorescence intensity per $OD_{660}$ (GFP/$OD_{660}$) of each of transformants and ARC032 strain in Example 3.

Every culture broth of the transformant after cultivation showed GFP fluorescence, indicating that each transformant produces EGFP. The results of calculation of $GFP/OD_{660}$ of each of the transformants and the ARC032 strain after cultivation, are shown in FIG. 7. With respect to the CMV promoter, in the same manner as in Example 1, a large EGFP production was confirmed in the strain using the ihc2 terminator. Such tendency was maintained with respect to the inch1 promoter and the hsp9 promoter, and also in a case were the EGFP production improved by use of the inch1 promoter or the hsp9 promoter, a larger EGFP production was observed in the strain using the ihc2 terminator. These results strongly suggest that the effect to improve the expression efficiency by using the ihc2 terminator is achieved regardless of the intensity of the promoter.

Example 4

Influences of the type of a protein over the effect to improve the expression efficiency by use of ihc2 terminator, were examined by using hPDI(abx) as a model secretory protein instead of EGFP. hPDI(abx) is a partial protein of PDI derived from human, composed of an a-domain, a b-domain and an x-domain of PDI derived from human.

<Production of hPDI1(abx) Secretory Expression Vector> (pPDI1 (SP)-hPDI(abx)-inv1t, pPDI1 (SP)-hPDI (abx)-ihc2t, pPDI1 (SP)-hPDI(abx)-nmt1 t)

hPDI1(abx) secretory expression vectors were respectively produced based on publicly-known hPDI1(abx) secretory expression vector pPDI1 (SP)-hPDI(abx) (WO2013/111754). pPDI1 (SP)-hPDI(abx) is a single-locus integration vector comprising a CMV promoter, a gene encoding *S. pombe* PDI1 signal peptide portion, and LPI terminator in a hPDI(abx) secretory expression cassette, for integrating the expression cassette into leu1 gene locus of *S. pombe*.

pPDI1 (SP)-hPDI (abx)-inv1t was produced as follows. pPDI1 (SP)-hPDI(abx) was subjected to double digestion with restriction enzymes XbaI and EcoRI to remove LPI terminator portion, and pSL12inv1t constructed in Example 3 was subjected to double digestion with restriction enzymes XbaI and EcoRI to recover inv1 terminator portion, and both digested products were ligated to each other for transforming *E. coli* DH5α to obtain a plasmid. The obtained plasmid was named as pPDI1(SP)-hPDI(abx)-inv1t.

pPDI1 (SP)-hPDI(abx)-ihc2t was produced as follows. pSL12ihc2t constructed in Example 3 was subjected to double digestion with restriction enzymes XbaI and EcoRI to recover ihc2 terminator portion, and the digested product and pPDI1(SP)-hPDI(abx) above double-digested with restriction enzymes XbaI and EcoRI were ligated to each other for transforming *E. coli* DH5α to obtain a plasmid. The obtained plasmid was named as pPDI1 (SP)-hPDI(abx)-ihc2t.

pPDI1 (SP)-hPDI(abx)-nmt1t was produced as follows. pPDI1 (SP)-hPDI(abx) was subjected to double digestion with restriction enzymes SbfI and PvuI to remove a DNA fragment containing LPI terminator and a top2 homologous recombination region, and pSL6EGFP-nmt1t constructed in Example 1 was subjected to double digestion with restriction enzymes SbfI and PvuI to recover a DNA fragment containing nmt1 terminator and a top2 homologous recombination region, and both digested products were ligated to each other for transforming *E. coli* DH5α to obtain a plasmid. The obtained plasmid was named as pPDI1 (SP)-hPDI(abx)-nmt1t.

<Host>

As the host, A8 strain (genotype: h⁻, leu1-32, ura4-D18, Δpsp3, Δisp6, Δoma1, Δppp16, Δfma2, Δsxa2, Δatg4, Δppp20) produced by deleting eight protease genes from the ARC001 strain of *S. pombe* was used. The A8 strain is a strain preliminarily constructed by gene replacement of the target ORF using a gene cassette (refer to WO2007/015470).

<Production of Transformant>

Using each of the produced expression vectors, in the same manner as in Example 1, transformants using A8 strain as a host were produced.

Transformants obtained by using hPDI1(abx) secretory expression vectors pPDI1 (SP)-hPDI(abx), pPDI1(SP)-hPDI (abx)-nmt1t, pPDI1 (SP)-hPDI(abx)-inv1 t and pPDI1 (SP)-hPDI(abx)-ihc2t, were named as hPDI(abx)/LPIt strain, hPDI(abx)/nmt1t strain, hPDI (abx)/inv1t strain and hPDI (abx)/ihc2t strain, respectively.

<Measurement of Amount of hPDI1(abx) Secreted>

Each of the above obtained transformants and non-expression A8 strain was inoculated in 5 ml of YPD+MES medium (1% of yeast extract, 1% of peptone, 2% of glucose and 0.3 M of 2-morpholinoethanesulfonic acid monohydrate) (pH 6.0) and cultivated for three days at 32° C. The culture broth was centrifuged to collect a culture supernatant, and a TCA (trichloroacetic acid) solution was added to 4 ml of the collected culture supernatant to a final concentration of 10% (w/w), followed by cooling to collect a precipitate. To the precipitate, 40 µl of a SDS-PAGE sample buffer was added, followed by incubation at 95° C. for 5 minutes to prepare a PAGE sample. 10 µl of the PAGE sample (corresponding to 1 ml of the culture supernatant) was applied on an acrylamide gel. After carrying out SDS-PAGE, the gel was subjected to CBB staining so as to detect the stained image by using Gel Doc (registered trademark) XR+system (manufactured by Bio-Rad Laboratories, Inc., USA). The detected secretary bands of hPDI1(abx) were quantified to calculate the relative amount of hPDI(abx) secreted from each transformant, where the amount of hPDI(abx) secreted from the hPDI(abx)/LPIt strain was set as 1.

Figure 8:
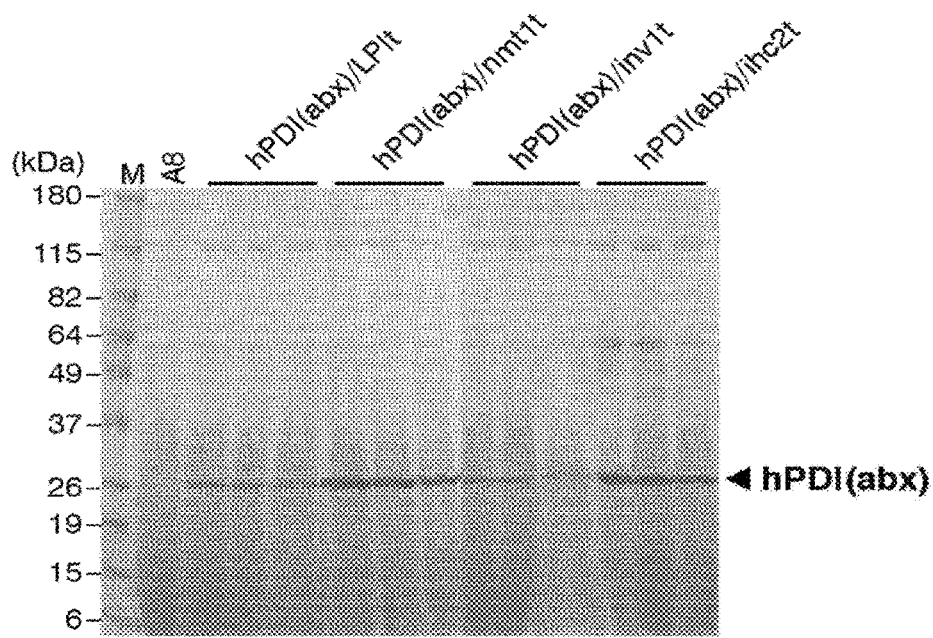
FIG. 8 is a CBB chromatic figure of a culture of each of transformants and A8 strain in Example 4.
Figure 9:
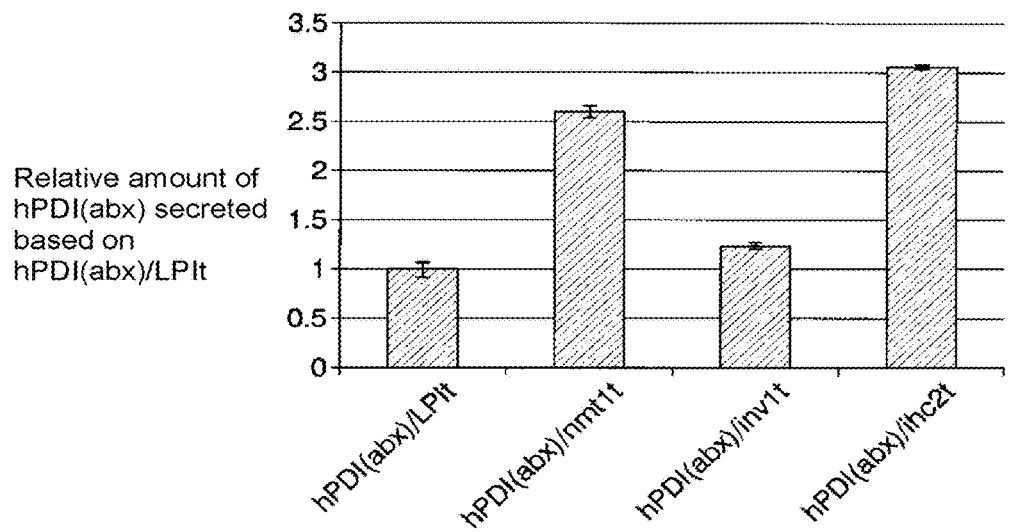
FIG. 9 is a graph illustrating results of calculation of the relative amount of hPDI(abx) secreted from each of transformants taking the amount of hPDI(abx) secreted from hPDI(abx)/LPIt strain being 1 in Example 4.

A CBB staining image is shown in FIG. 8, and the results of calculation of the relative amount of hPDI(abx) secreted from each transformant, are shown in FIG. 9. As shown in FIG. 8, secretion of hPDI(abx) from all the transformants was confirmed. From the results shown in FIG. 9, the amount of hPDI(abx) secreted from the hPDI (abx)/inv1t strain was equal to or slightly improved as compared with the hPDI(abx)/LPIt strain. On the other hand, the amount of hPDI(abx) secreted from the hPDI(abx)/nmt1t strain improved about 2.5 times that secreted from hPDI(abx)/LPIt strain, and the amount secreted from the hPDI(abx)/ihc2t strain improved about 3 times that secreted from the hPDI (abx)/LPIt strain. The fact that the ihc2 terminator improved the production of EGFP suggests that the effect to improve the expression efficiency is achieved by the ihc2 terminator regardless of the type of the protein.

Example 5

By stepwise shortening the region downstream from ihc2 gene ORF, the ihc2 gene terminator region was studied.
(Production of Transformant by Gap-repair Cloning)

An EGFP expression cassette having terminator derived from an ihc2 gene with various lengths disposed downstream from a structural gene encoding an EGFP gene, was integrated into leu1 gene locus of S. pombe utilizing gap-repair cloning. The gap-repair cloning is a method in which utilizing recombinational repair of a yeast, homologous recombination of DNA fragments having a homologous region of 20 to 30 bp at their terminals is brought about in a cell of the yeast to connect the DNA fragments.

Specifically, PCR was carried out by using pSL6EGFP-LPIt as a template, and a combination of a forward primer composed of a nucleotide sequence of SEQ ID NO: 46, and a reverse primer composed of a nucleotide sequence of SEQ ID NO: 47, and a combination of a forward primer composed of a nucleotide sequence of SEQ ID NO: 48 and a reverse primer composed of a nucleotide sequence of SEQ ID NO: 49, thereby to obtain a PCR product (leu1+hCMVp+EGFP fragment) and a PCR product (top2 fragment) each comprising a part of leu1 gene, hCMV promoter and the EGFP gene, respectively.

Further, PCR was carried out by using a genomic DNA derived from a wild-type strain (ARC032 strain) of S. pombe as a template, a forward primer comprising a homologous region 24 bp to the 3' end of the leu1+hCMVp+EGFP fragment at the 5' end and a reverse primer comprising a homologous region 24bp to the 5' end of the top2 fragment at the 5' end, thereby to obtain a PCR product of a downstream region of an ihc2 gene having a homologous region 24 bp to the 3' end of the leu1 +hCMVp+EGFP fragment at the 5' end, and a homologous region 24 bp to the 5' end of the top2 fragment at the 3' end, in the following combination of primers. Specifically, a PCR product (ihc2t(525) fragment) with a downstream region length of the ihc2 gene of 525 bp (a region 1 to 525 bp downstream from the 3' end of the ORF, that is, a region 1st to 525th in SEQ ID NO: 19) was obtained by carrying out PCR by using a combination of a forward primer composed of a nucleotide sequence of SEQ ID NO: 50 and a reverse primer composed of a nucleotide sequence of SEQ ID NO: 51, a PCR product (ihc2t(400) fragment) with the length being 400 bp (a region 1 to 400 bp downstream from the 3' end of the ORF, that is, a region 1st to 400th in SEQ ID NO: 19) was obtained by carrying out PCR by using a combination of a forward primer composed of a nucleotide sequence of SEQ ID NO: 50 and a reverse primer composed of a nucleotide sequence of SEQ ID NO: 52, a PCR product (ihc2t(300) fragment) with the length being 300 bp (a region 1 to 300 bp downstream from the 3' end of the ORF, that is, a region 1st to 300th in SEQ ID NO: 19) was obtained by carrying out PCR by using a combination of a forward primer composed of a nucleotide sequence of SEQ ID NO: 50 and a reverse primer composed of a nucleotide sequence of SEQ ID NO: 53, a PCR product (ihc2t(200) fragment) with the length being 200 bp (a region 1 to 200 bp downstream from the 3' end of the ORF, that is, a region 1st to 200th in SEQ ID NO: 19) was obtained by carrying out PCR by using a combination of a forward primer composed of a nucleotide sequence of SEQ ID NO: 50 and a reverse primer composed of a nucleotide sequence of SEQ ID NO: 54, a PCR product (ihc2t(175) fragment) with the length being 175 bp (a region 1 to 175 bp downstream from the 3' end of the ORF, that is, a region 1st to 175th in SEQ ID NO: 19) was obtained by carrying out PCR by using a combination of a forward primer composed of a nucleotide sequence of SEQ ID NO: 50 and a reverse primer composed of a nucleotide sequence of SEQ ID NO: 55, a PCR product (ihc2t(150) fragment) with the length being 150 bp (a region 1 to 150 bp downstream from the 3' end of the ORF, that is, a region 1st to 150th in SEQ ID NO: 19) was obtained by carrying out PCR by using a combination of a forward primer composed of a nucleotide sequence of SEQ ID NO: 50 and a reverse primer composed of a nucleotide sequence of SEQ ID NO: 56, a PCR product (ihc2t(125) fragment) with the length being 125 bp (a region 1 to 125 bp downstream from the 3' end of the ORF, that is, a region 1st to 125th in SEQ ID NO: 19) was obtained by carrying out PCR by using a combination of a forward primer composed of a nucleotide sequence of SEQ ID NO: 50 and a reverse primer composed of a nucleotide sequence of SEQ ID NO: 57, and a PCR product (ihc2t(100) fragment) with the length being 525 bp (a region 1 to 100 bp downstream from the 3' end of the ORF, that is, a region 1st to 100th in SEQ ID NO: 19) was obtained by carrying out PCR by using a combination of a forward primer composed of a nucleotide sequence of SEQ ID NO: 50 and a reverse primer composed of a nucleotide sequence of SEQ ID NO: 58.

Transformants were obtained in the same manner as in (Production of transformant) in Example 1 by adding the above obtained PCR products instead of each EGFP expression vector digested with the restriction enzyme NotI. A transformant obtained by adding leu1 +hCMVp+EGFPfragment, top2 fragment and ihc2t(525) fragment was named as ihc2t(525) strain, a transformant obtained by adding leu1 +hCMVp+EGFP fragment, top2 fragment and ihc2t(400) fragment was named as ihc2t(400) strain, a transformant obtained by adding leu1 +hCMVp+EGFP fragment, top2 fragment and ihc2t(300) fragment was named as ihc2t(300) strain, a transformant obtained by adding leu1 +hCMVp+EGFP fragment, top2 fragment and ihc2t(200) fragment was named as ihc2t(200) strain, a transformant obtained by adding leu1 +hCMVp+EGFP fragment, top2 fragment and ihc2t(175) fragment was named as ihc2t(175) strain, a transformant obtained by adding leu1+hCMVp+EGFP fragment, top2 fragment and ihc2t(150) fragment was named as ihc2t(150) strain, a transformant obtained by adding leu1 +hCMVp+EGFP fragment, top2 fragment and ihc2t(125) fragment was named as ihc2t(125) strain, and a transformant obtained by adding leu1 +hCMVp+EGFP fragment, top2 fragment and ihc2t(100) fragment was named as ihc2t(100) strain.

<Measurement of GFP Fluorescence Intensity of Cells>

Figure 10:
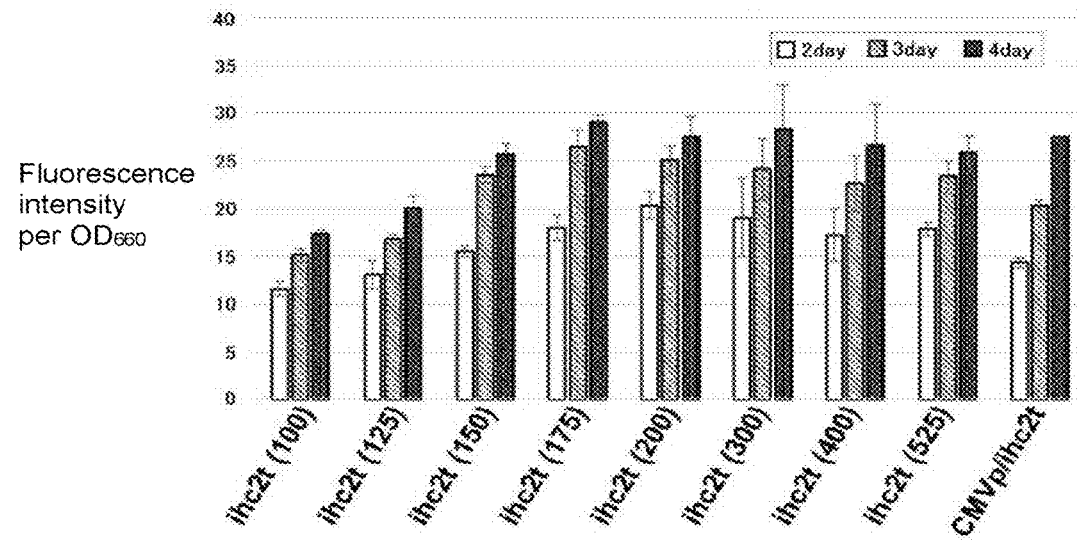
FIG. 10 is a graph illustrating results of calculation of GFP fluorescence intensity per $OD_{660}$ of each of transformants in Example 5.

Each of the CMVp/ihc2t strain which is the transformant obtained in Example 1 and the above obtained transformants was inoculated in 5 ml of EMM medium in a test tube, and cultivated at 32° C. for 4 days. The downstream region length of the ihc2 gene in the EGFP expression cassette of the CMVp/ihc2t strain is 625 bp. The cell-density ($OD_{660}$) and the GFP fluorescence intensity (excitation wavelength: 490 nm, fluorescence wavelength: 530 nm) of each culture broth 2 to 4 days after cultivation were measured by MTP-810Lab to calculate the GFP fluorescence intensity per $OD_{660}$ (GFP/$OD_{660}$) of each transformant. The results are shown in FIG. 10. When the downstream region length of the ihc2 gene is from 175 to 625bp, there was no substantial difference in the GFP fluorescence intensity, and each downstream region showed an equal terminator activity. On the other hand, as the downstream region length of the ihc2 gene becomes shorter than 175 bp, the GFP fluorescence intensity decreased. These results indicate that the terminator activity is gradually lost as the downstream region length of the ihc2 gene becomes shorter than 175bp.

What is claimed is:

1. A cloning vector comprising a promoter capable of functioning in a yeast of the genus *Schizosaccharomyces*, a cloning site for introducing a foreign structural gene which is located downstream from the promoter and is regulated by the promoter, and ihc2 gene terminator of the yeast of the genus *Schizosaccharomyces*.

2. The cloning vector according to claim 1, wherein the ihc2 gene terminator is a region 1 to 625 bp downstream from the 3' end of ihc2 gene ORF (open reading frame).

3. The cloning vector according to claim 1, wherein the ihc2 gene is a gene of *Schizosaccharomyces pombe*.

4. The cloning vector according to claim 1, wherein the ihc2 gene terminator comprises the nucleotide sequence of SEQ ID NO:19 or a nucleotide sequence having substitution, deletion or addition of at least one nucleotide in the nucleotide sequence of SEQ ID NO: 19, and has a terminator activity for the ihc2 gene of the yeast of the genus *Schizosaccharomyces*.

5. The cloning vector according to claim 1, wherein the ihc2 gene terminator comprises a nucleotide sequence having at least 80% homology with the nucleotide sequence of SEQ ID NO: 19 and has a terminator activity for the ihc2 gene of the yeast of the genus *Schizosaccharomyces*.

6. An expression vector comprising a promoter capable of functioning in a yeast of the genus *Schizosaccharomyces*, a foreign structural gene which is located downstream from the promoter and is regulated by the promoter, and ihc2 gene terminator of the yeast of the genus *Schizosaccharomyces*.

7. The expression vector according to claim 6, wherein the ihc2 gene terminator is a region 1 to 625 bp downstream from the 3' end of ihc2 gene ORF (open reading frame).

8. The expression vector according to claim 6, wherein the ihc2 gene is a gene of *Schizosaccharomyces pombe*.

9. A method for producing an expression vector, comprising:
   introducing a foreign structural gene into the cloning site of the cloning vector of claim 1.

10. A method for producing an expression vector, comprising:
    replacing a terminator in an expression vector comprising a promoter capable of functioning in a yeast of the genus *Schizosaccharomyces*, a foreign structural gene which is located downstream from the promoter and is regulated by the promoter, and the terminator with ihc2 gene terminator of the yeast of the genus *Schizosaccharomyces*,
wherein the terminator in the expression vector is different from the ihc2 gene terminator.

11. A method for producing an expression vector, comprising:
introducing a foreign structural gene into the cloning site of the cloning vector of claim 2.

12. A method for producing an expression vector, comprising:
introducing a foreign structural gene into the cloning site of the cloning vector of claim 3.

13. A transformant of a yeast of the genus *Schizosaccharomyces*, comprising an expression cassette containing a promoter capable of functioning in the yeast of the genus *Schizosaccharomyces*, a foreign structural gene which is located downstream from the promoter and is regulated by the promoter, and ihc2 gene terminator of the yeast of the genus *Schizosaccharomyces*.

14. The transformant according to claim 13, which has an expression vector containing the expression cassette outside its chromosome.

15. The transformant according to claim 13, which has the expression cassette in its chromosome.

16. The transformant according to claim 13, wherein the ihc2 gene terminator is a region 1 to 625 bp downstream from the 3' end of ihc2 gene ORF (open reading frame).

17. The transformant according to claim 13, wherein the ihc2 gene is a gene of *Schizosaccharomyces pombe*.

18. A method for producing the transformant as defined in claim 13, which comprises making an expression vector containing the expression cassette be maintained outside a chromosome of a yeast of the genus *Schizosaccharomyces*.

19. A method for producing the transformant of claim 13, comprising:
introducing an expression vector containing the expression cassette into a chromosome of a yeast of the genus *Schizosaccharomyces*.

20. A method for producing a protein, comprising:
cultivating the transformant of claim 13, and
recovering a protein encoded by the foreign structural gene from cells or a culture supernatant obtained by the clutivating.

* * * * *

SEQUENCE LISTING

<160> NUMBER OF SEQ ID NOS: 58

<210> SEQ ID NO 1
<211> LENGTH: 720
<212> TYPE: DNA
<213> ORGANISM: Artificial Sequence
<220> FEATURE:
<223> OTHER INFORMATION: Description of Artificial Sequence: EGFP gene

<400> SEQUENCE: 1

```
atggtgagca agggcgagga gctgttcacc ggggtggtgc ccatcctggt cgagctggac      60
ggcgacgtaa acggccacaa gttcagcgtg tccggcgagg gcgagggcga tgccacctac     120
ggcaagctga ccctgaagtt catctgcacc accggcaagc tgcccgtgcc ctggcccacc     180
ctcgtgacca ccctgaccta cggcgtgcag tgcttcagcc gctaccccga ccacatgaag     240
cagcacgact tcttcaagtc cgccatgccc gaaggctacg tccaggagcg caccatcttc     300
ttcaaggacg acggcaacta caagacccgc gccgaggtga agttcgaggg cgacaccctg     360
gtgaaccgca tcgagctgaa gggcatcgac ttcaaggagg acggcaacat cctggggcac     420
aagctggagt acaactacaa cagccacaac gtctatatca tggccgacaa gcagaagaac     480
ggcatcaagg tgaacttcaa gatccgccac aacatcgagg acggcagcgt gcagctcgcc     540
gaccactacc agcagaacac ccccatcggc gacggccccg tgctgctgcc cgacaaccac     600
tacctgagca cccagtccgc cctgagcaaa gaccccaacg agaagcgcga tcacatggtc     660
ctgctggagt tcgtgaccgc cgccgggatc actctcggca tggacgagct gtacaagtaa     720
```

<210> SEQ ID NO 2
<211> LENGTH: 23
<212> TYPE: DNA
<213> ORGANISM: Artificial Sequence
<220> FEATURE:
<223> OTHER INFORMATION: Description of Artificial Sequence: Forward primer

<400> SEQUENCE: 2

```
ggaccatggt gagcaagggc gag                                              23
```

<210> SEQ ID NO 3
<211> LENGTH: 31
<212> TYPE: DNA
<213> ORGANISM: Artificial Sequence
<220> FEATURE:
<223> OTHER INFORMATION: Description of Artificial Sequence: Reverse primer

<400> SEQUENCE: 3

```
ggacctgcag gttacttgta cagctcgtcc a                                     31
```

<210> SEQ ID NO 4
<211> LENGTH: 548

```
<212> TYPE: DNA
<213> ORGANISM: Schizosaccharomyces pombe
<220> FEATURE:
<223> OTHER INFORMATION: inv1 terminator

<400> SEQUENCE: 4
atattttgtt tcaagttagg aaagtataat aacttttgtc cctgcatatt caattgtaaa      60
gtttagttta ccttttcatc gtaaccacaa ttgtcaccta aatctctaaa aatctcttca     120
cttatctagt taatgtcgta acaaaaaagt ccagtagctt cgggaaatga tgcttggaat     180
catacaagtc gacgtgggtt ttcccttcaa caatgtacag ctcttttggc tcggaagcga     240
cagcatatgc ttcctttgaa aaatacagag tgtcagcctt ctcaccagct atgtacaaca     300
aaggcctagg agccatttgt ttaagaacat ccgtggctcc ataaaagcca gccaataact     360
ccatgctcca cggctggaaa ataccggtgg atcgaggatg ggaaccacgc ggtgtacaat     420
aatagtcata ggcttctttg aataataatg gggtggcatc agacaattgc tctctttggg     480
ggataaaatt gaacaagtca tatgactcac ccttacaaat ttggttcgcg aggcagcggc     540
accttcta                                                              548

<210> SEQ ID NO 5
<211> LENGTH: 27
<212> TYPE: DNA
<213> ORGANISM: Artificial Sequence
<220> FEATURE:
<223> OTHER INFORMATION: Description of Artificial Sequence: Forward
      primer

<400> SEQUENCE: 5
tcctgcagaa ggaatgtctc ccttgcc                                          27

<210> SEQ ID NO 6
<211> LENGTH: 30
<212> TYPE: DNA
<213> ORGANISM: Artificial Sequence
<220> FEATURE:
<223> OTHER INFORMATION: Description of Artificial Sequence: Reverse
      primer

<400> SEQUENCE: 6
ctggaattcc cacatgctgt aaacaaagtc                                       30

<210> SEQ ID NO 7
<211> LENGTH: 573
<212> TYPE: DNA
<213> ORGANISM: Schizosaccharomyces pombe
<220> FEATURE:
<223> OTHER INFORMATION: nmt1 terminator

<400> SEQUENCE: 7
aaggaatgtc tcccttgcca gtactgctag ggttttttctt tcaaactatg gaagcccatt      60
caagctgcat attacgattt tgttttttcgc ttttagaaag tggtttagat gagataaatag    120 aaaaattctt gatctccgac aacgagtact tttatttttt ttgctaatca ctttactcaa     180
tattagctcg aaatcgtaga aacgtagacg ggtgcgggat accgagtggt gtagttaaga    240 attttttataa accacgtggc ccaaaaatat gaacccaaaa cgtttataca tgagtatact    300
ttaagaaggc tatacccctt cgtgttagat gtagttttag ctacccaacc cgagtctatg    360
agcttgactt cagatgtaga aggcattaaa tcgtttgaa tattaattaa aaaacgatga     420
aaattaaata tttaaaagca atcatacgct gaaaatttag tgctgtggct aatccttcaa    480
```

```
catggaaatg ccataaaagt gactttgaca aaaaaaaaag tatatacagg tagtaaactc      540
atctacttca ttgactttgt ttacagcatg tgg                                  573
```

<210> SEQ ID NO 8
<211> LENGTH: 36
<212> TYPE: DNA
<213> ORGANISM: Artificial Sequence
<220> FEATURE:
<223> OTHER INFORMATION: Description of Artificial Sequence: Forward
      primer

<400> SEQUENCE: 8

```
tcctgcagag aggttcttat gacttaaaat tcatgc                               36
```

<210> SEQ ID NO 9
<211> LENGTH: 28
<212> TYPE: DNA
<213> ORGANISM: Artificial Sequence
<220> FEATURE:
<223> OTHER INFORMATION: Description of Artificial Sequence: Reverse
      primer

<400> SEQUENCE: 9

```
ggactagtcg ttgtttctat caccatcc                                        28
```

<210> SEQ ID NO 10
<211> LENGTH: 545
<212> TYPE: DNA
<213> ORGANISM: Schizosaccharomyces pombe
<220> FEATURE:
<223> OTHER INFORMATION: hsp9 terminator

<400> SEQUENCE: 10

```
agaggttctt atgacttaaa attcatgctt ttggctggtg aaactcaatc caccaaagca      60
tcgggatgat ttctttaccg atgaacggac gaaaatggtt tgaggtctcc tcaatttagt     120
aggtagtggt tggattgttt ttatgaacga tccatctcat cactttctaa tgcgaggttg     180
catccttgac caattaccat ctaattttat gatatataac gaggttacgt gataccatca     240
tatatatata tttgctcgac ttttttttaca aattttttc aaaagtggg tgcttatata      300 ttctttggtt caaaatcttt atcgatttga agtaatgaaa tatattttcc cttatccct      360 atatactttt tactaccata tctagcaact gtattgttta catataagta acgagtaact     420
taaaaacagt actgtaaaac agttagtagt tgtgacttgg gtaacaagtg ttttcatcca     480
ctgtttgaca taggaatgtt acaatgatga aaactcaaaa cattaggatg gtgatagaaa     540
caacg                                                                 545
```

<210> SEQ ID NO 11
<211> LENGTH: 33
<212> TYPE: DNA
<213> ORGANISM: Artificial Sequence
<220> FEATURE:
<223> OTHER INFORMATION: Description of Artificial Sequence: Forward
      primer

<400> SEQUENCE: 11

```
tcctgcagaa tcgtctcttc cgattttaat atg                                  33
```

<210> SEQ ID NO 12
<211> LENGTH: 32
<212> TYPE: DNA
<213> ORGANISM: Artificial Sequence
<220> FEATURE:

<223> OTHER INFORMATION: Description of Artificial Sequence: Reverse
primer

<400> SEQUENCE: 12
ctggaattcc aaaaggaaga cgatttcatt gc    32

<210> SEQ ID NO 13
<211> LENGTH: 527
<212> TYPE: DNA
<213> ORGANISM: Schizosaccharomyces pombe
<220> FEATURE:
<223> OTHER INFORMATION: hsp16 terminator

<400> SEQUENCE: 13
aatcgtctct tccgatttta atatgatagt ttcgaaatgg ttatgagacc aatcttgttg    60
gattgtgagc atatattatt gtttgattta acaatcaatc ataacatatg caattaatga   120
tccgcttgcc attggattga tgaattttga taatgaattg aacacggtct tctaaacagt   180
aaaagagcat ttaaattcca catcaagcaa tttatggcca gctgtcagac agtgttttaa   240
tgatcttgac taccacttgt tacgattctc caatgatgag caagtgatct ctagcaattt   300
ttcaaaataa ataaataaat aaatattttt ttattcctaa ttagaaaaca agttgtttca   360
aaatgctcta tcgtaatatg tgtagattta tttttatttt tttcaaaaaa aaagaacagt   420
attatgtagc tcctaatgaa ttaacaggag ttacattagc atatcataaa gttgtgtatg   480
ctctttgagt cttaaatcac cggggcaatg aaatcgtctt ccttttg                 527

<210> SEQ ID NO 14
<211> LENGTH: 27
<212> TYPE: DNA
<213> ORGANISM: Artificial Sequence
<220> FEATURE:
<223> OTHER INFORMATION: Description of Artificial Sequence: Forward
primer

<400> SEQUENCE: 14
tcctgcagtt gctgcccagt tgattac    27

<210> SEQ ID NO 15
<211> LENGTH: 28
<212> TYPE: DNA
<213> ORGANISM: Artificial Sequence
<220> FEATURE:
<223> OTHER INFORMATION: Description of Artificial Sequence: Reverse
primer

<400> SEQUENCE: 15
ggactagttc cttcatcttc tagacgtg    28

<210> SEQ ID NO 16
<211> LENGTH: 520
<212> TYPE: DNA
<213> ORGANISM: Schizosaccharomyces pombe
<220> FEATURE:
<223> OTHER INFORMATION: ihc1 terminator

<400> SEQUENCE: 16
ttgctgccca gttgattacc cgtcattgct ttgatgtgtc tgaagtatct tcagttttga    60
ttttatgttg ttaatacaga attccatagt aatgatgagt atacatgttt atgatcttat   120
gaatattatt tcattcacca gcttttaact tttgaaaccg ttgtccttgt agaagtagtc   180
gacaccccat agcatacaat taaaacgatt ctcctaagat ttgcatacac aaacgttatt   240

```
gtatttatct taatatctgt tgcgtcgata tcggccgcca gaacctctag aggagtagtt        300
ggagtatctg tccggagatg gttttcgcct tgatgaggaa ggatagttgc tactgtgagg        360
atggttacta ggaggtcttg aggcattata gttcgtagag gctccattcc cataactcga        420
tgtaggatta tgagtaggtt gtgcatgcgt cataccagca ctcgatgtaa tattagggga        480
attcgctgga ctttcacttt cacgtctaga agatgaagga                              520

<210> SEQ ID NO 17
<211> LENGTH: 40
<212> TYPE: DNA
<213> ORGANISM: Artificial Sequence
<220> FEATURE:
<223> OTHER INFORMATION: Description of Artificial Sequence: Forward
      primer

<400> SEQUENCE: 17
tcctgcagaa taaagcaacg aactaaacga aatttattgc                              40

<210> SEQ ID NO 18
<211> LENGTH: 34
<212> TYPE: DNA
<213> ORGANISM: Artificial Sequence
<220> FEATURE:
<223> OTHER INFORMATION: Description of Artificial Sequence: Reverse
      primer

<400> SEQUENCE: 18
ctggaattcg aatagattgt aaccacttag ggag                                    34

<210> SEQ ID NO 19
<211> LENGTH: 625
<212> TYPE: DNA
<213> ORGANISM: Schizosaccharomyces pombe
<220> FEATURE:
<223> OTHER INFORMATION: ihc2 terminator

<400> SEQUENCE: 19
aataaagcaa cgaactaaac gaaatttatt gcttctaact ttaactttt  ggcaagctat        60 gatgttcaca agctgtcata gcttatttta cgatttcacc cttatatatt tttaatgaga       120
tttcaatcac attaaaatac atgtctttat ttttataggc agtttgttca tgcatatatg       180
tagttttgta tttccttcga acagcettaa ttgatgtagc agttacttt  taatggaatt       240 gtgtagttgc cttgttaatt tctcattacg acaaggttgt gttgtgtaaa tactcttttc       300
tttagtaaac aatacgcgtc atactaaggg taagtaccat tattatggtg tatcacttgt       360
aactttcagt acagctaatt cttcacatt  accaatagca aaccggtcta aaaaacatct       420
attatgacaa taaaaagctc cgaacttctg aaaagaatga ctgcatatga atgtgaaatt       480
aaaaaaaata tcaacactac ttcttaatga atgtattact ttggttctag gaaaatcaaa       540
atgatatagt attacaaatt aatcaatata ttattcagtg ttgttttgc  atgttaatat       600 ctccctaagt ggttacaatc tattc                                             625

<210> SEQ ID NO 20
<211> LENGTH: 27
<212> TYPE: DNA
<213> ORGANISM: Artificial Sequence
<220> FEATURE:
<223> OTHER INFORMATION: Description of Artificial Sequence: Forward
      primer

<400> SEQUENCE: 20
```

```
tcctgcaggg gaatgagaat gtgatcc                                          27

<210> SEQ ID NO 21
<211> LENGTH: 34
<212> TYPE: DNA
<213> ORGANISM: Artificial Sequence
<220> FEATURE:
<223> OTHER INFORMATION: Description of Artificial Sequence: Reverse
      primer

<400> SEQUENCE: 21
ctggaattcc acttttggat gtcttacact taac                                  34

<210> SEQ ID NO 22
<211> LENGTH: 528
<212> TYPE: DNA
<213> ORGANISM: Schizosaccharomyces pombe
<220> FEATURE:
<223> OTHER INFORMATION: adh1 terminator

<400> SEQUENCE: 22
gggaatgaga atgtgatcca cttttaattc ctaatgaata catgcctata gttcttttct       60
tttgttcttt atgtcgtttt tcgatggtac ggccgttgtc aatctcagtt tgtgtgcttg      120
gttgcagctt ggtttcaaat ctgttcatct catgaatctt ttaccatttc accacacgtt      180
tataccattc tctcatagaa tcttcatcaa accatctcgg ggttagagtg gaaagaaagt      240
cttgttcttt tatttccttt tttccatctt caaggctttt cttttcttcc tcctcctcgt      300
tcatcttgag gtttgacgtg tctgtttaga attttgagct gttgcagcat cttatttttt      360
gttttgcgaa aacgaagcgc tttactctct tcatcagttg gacgattgta cctttgaaaa      420
ccaactactt tgcatgtttt tgtatagaaa tcaatgatat tagaatccca tcctttaatt      480
tctttcaaag tagttgagct atagttaagt gtaagacatc caaaagtg                   528

<210> SEQ ID NO 23
<211> LENGTH: 30
<212> TYPE: DNA
<213> ORGANISM: Artificial Sequence
<220> FEATURE:
<223> OTHER INFORMATION: Description of Artificial Sequence: Forward
      primer

<400> SEQUENCE: 23
tcctgcaggc tcctcttact ttttgtaacg                                       30

<210> SEQ ID NO 24
<211> LENGTH: 26
<212> TYPE: DNA
<213> ORGANISM: Artificial Sequence
<220> FEATURE:
<223> OTHER INFORMATION: Description of Artificial Sequence: Reverse
      primer

<400> SEQUENCE: 24
ctggaattcc catctcctac agcttc                                           26

<210> SEQ ID NO 25
<211> LENGTH: 783
<212> TYPE: DNA
<213> ORGANISM: Schizosaccharomyces pombe
<220> FEATURE:
<223> OTHER INFORMATION: act1 terminator

<400> SEQUENCE: 25
```

```
gctcctctta cttttttgtaa cgttttttac atactttttga ataacatcga ttcttctgat    60
atatataaat ttcaatcttt ttttacctat ttaaccacct ttttccgctc ttaacatctc    120
atgaggaact ttgggtatca attattggag tgttttatat actttctgat tactatcgtt    180
ttcttgctct gttttctttt tttcattata gacgaatgca gagctagcct tttacatatt    240
gaagttacag aaatatttcc agtagatacc tatgatgtta cttcattcgc ttataacttc    300
ccgttttctt taacatgttt cttctcgagt ccggccgatt attttttgtcg atattttcgt    360 tatgtttatc gctgtgatta tcgattaaag aactgtagta aatgaatttt acttactccc    420
gttaattttt acgaatttta ttttgtacaa ggtggtaact gcgagatagt tagaagcgga    480
agtggtgcaa tgtacttcat cagccatttc ttttcgtcct gtagagttgt atcatcttca    540
gtactgattt aattggtacc tgaacttgta aactttgaa gccaaatggt tgaatgtgtt     600
ttacattagt attagcaaaa gtttattagg tcaaaaaaag atttaataca tacatggtat    660
atgatcattg ttggatagta tagttgaggt aaaattctta taaattgtaa gacattggta    720
tgattagtgt tcttcaaata taaaagaga ggaagtagtg aattatgaag ctgtaggaga     780
tgg                                                                    783
```

<210> SEQ ID NO 26
<211> LENGTH: 43
<212> TYPE: DNA
<213> ORGANISM: Artificial Sequence
<220> FEATURE:
<223> OTHER INFORMATION: Description of Artificial Sequence: Forward
       primer

<400> SEQUENCE: 26

```
tcctgcagag tgttttaaaa ttgcctgtac tttcattttt aag                         43
```

<210> SEQ ID NO 27
<211> LENGTH: 30
<212> TYPE: DNA
<213> ORGANISM: Artificial Sequence
<220> FEATURE:
<223> OTHER INFORMATION: Description of Artificial Sequence: Reverse
       primer

<400> SEQUENCE: 27

```
ctggaattcc actacagctt attttcgtcc                                        30
```

<210> SEQ ID NO 28
<211> LENGTH: 719
<212> TYPE: DNA
<213> ORGANISM: Schizosaccharomyces pombe
<220> FEATURE:
<223> OTHER INFORMATION: bip1 terminator

<400> SEQUENCE: 28

```
agtgttttaa aattgcctgt actttcattt ttaagcttta cttagtatt tatttatgtc      60 gaagtatacg caagtctgac tcgatgctct cattgtttca tgaccttaat ctaagggtt     120 atttggaaac ccaaaatgtt ttctcatgat tattaatgtg gtctgatggc gttatcattt    180
tgatagcttc tcgagctgtt tctgctatct tgaaatgagt gttctctttt cattgttgaa    240
cgtcttgagt atgattaaaa tggtattatg tctccaaaat agacctgata taaagtgcat    300 tttacttat ctaccagaat cgtgactcta tagccattaa caaagttgta tgtcaacacc     360
tagttaactg gtgctttgtt atctttgtat tgcttacttc tgctaatggc tttgtggaac    420
tgacaataat tggtagttaa tcataaagac cctgtatgtt tatcaaattt tatagcattg    480
```

```
ggtactaatt ccttttatta taaatacaat cgttcttta tcttagtgtt tatacttacc      540
tgagtttgtg agtagcagct tttttatata tagtttaaa agtattctat ttattaaaac      600
atctcatttg attaagtcga agtgcaaagt ggtgaaattt tatggtgttg tgtatatttt     660
aaaattgctt tacttcaaaa acttagaatt tgttttttgg acgaaaataa gctgtagtg      719
```

<210> SEQ ID NO 29
<211> LENGTH: 45
<212> TYPE: DNA
<213> ORGANISM: Artificial Sequence
<220> FEATURE:
<223> OTHER INFORMATION: Description of Artificial Sequence: Forward
      primer

<400> SEQUENCE: 29

```
tcctgcagaa aaagactaat gtaaaatttt tttggttggt tattg                     45
```

<210> SEQ ID NO 30
<211> LENGTH: 31
<212> TYPE: DNA
<213> ORGANISM: Artificial Sequence
<220> FEATURE:
<223> OTHER INFORMATION: Description of Artificial Sequence: Reverse
      primer

<400> SEQUENCE: 30

```
ctggaattcc ttaagaacat gtgattggag c                                    31
```

<210> SEQ ID NO 31
<211> LENGTH: 529
<212> TYPE: DNA
<213> ORGANISM: Schizosaccharomyces pombe
<220> FEATURE:
<223> OTHER INFORMATION: ura4 terminator

<400> SEQUENCE: 31

```
aaaaagacta atgtaaaatt tttttggttg gttattgaaa aagtcgatgc cttgtttgcg      60
tttgttttcc taggcgtttt atgtcagaag gcatttagaa ttagtataca agtactcttt     120
ggtaaaattt tatgtagcga ctaaaatatt aactattata gataaacacc ttgggaataa     180
aaagtaattt gctatagtaa tttattaaac atgctcctac aacattacca caatcttttc     240
tcttggattg acattgaata agaaaagagt gaatttttt agacttgtaa tgataactat      300
gtacaaagcc aatgaaagat gtatgtagat gaatgtaaaa taccatgtag acaaacaaga     360
taaaacttgg ttataaacat tggtgttgga acagaataaa ttagatgtca aaaagtttcg     420
tcaatatcac aagctttatt attcaaaact agtatacttt ttctcggagt ataatacaca     480
atatcggtgc aaataggttt taaaattgct ccaatcacat gttcttaag                 529
```

<210> SEQ ID NO 32
<211> LENGTH: 47
<212> TYPE: DNA
<213> ORGANISM: Artificial Sequence
<220> FEATURE:
<223> OTHER INFORMATION: Description of Artificial Sequence: Forward
      primer

<400> SEQUENCE: 32

```
tcctgcagta gggtttaatg tagaataaat tcatatgatt tgatttg                   47
```

<210> SEQ ID NO 33
<211> LENGTH: 27

```
<212> TYPE: DNA
<213> ORGANISM: Artificial Sequence
<220> FEATURE:
<223> OTHER INFORMATION: Description of Artificial Sequence: Reverse
      primer

<400> SEQUENCE: 33
ctggaattcg tgctaacact gatgcag                                        27

<210> SEQ ID NO 34
<211> LENGTH: 516
<212> TYPE: DNA
<213> ORGANISM: Schizosaccharomyces pombe
<220> FEATURE:
<223> OTHER INFORMATION: leu1 terminator

<400> SEQUENCE: 34
tagggtttaa tgtagaataa attcatatga tttgatttga cctaatttttt attgattaat    60 tgtgtcgcat atttattatc gttaaaaatg caattgacaa aagcgtaaat tttaaggctc   120
taatgttttt tcttttggta tgttatagtc aagcaaagat gtattaagtt gcaaaagcat   180
ggaattgatt tacgacatcc gttcaacttt atgaccgagt tgtcgctgtg tacttactct   240
ttttttacta tgaaaagttt caaacataat atcattaatt atttcttttt aaacgaagta   300
acctgtaaca taataatag gggaaaagaa gaaaaaaacc ataaaaattc gagaacgtaa    360
caattattat tgtaacgatg acaacccgat tctttgagag agccagagac atgacttttg   420
cattaccgta attggtttct acttatgaat tgtaaacttg tgtagggaat tcatccaca    480 gctatcgcgg gctgctctct gcatcagtgt tagcac                             516

<210> SEQ ID NO 35
<211> LENGTH: 27
<212> TYPE: DNA
<213> ORGANISM: Artificial Sequence
<220> FEATURE:
<223> OTHER INFORMATION: Description of Artificial Sequence: Forward
      primer

<400> SEQUENCE: 35
tcctgcaggc gaccatagac ataactg                                        27

<210> SEQ ID NO 36
<211> LENGTH: 26
<212> TYPE: DNA
<213> ORGANISM: Artificial Sequence
<220> FEATURE:
<223> OTHER INFORMATION: Description of Artificial Sequence: Reverse
      primer

<400> SEQUENCE: 36
caatgcataa actcattgaa ttctcc                                         26

<210> SEQ ID NO 37
<211> LENGTH: 416
<212> TYPE: DNA
<213> ORGANISM: Schizosaccharomyces pombe
<220> FEATURE:
<223> OTHER INFORMATION: ade6 terminator

<400> SEQUENCE: 37
gcgaccatag acataactgt taatgattt tgcttgcttt ttgttttaaa taatattta      60 ttttgaaatt ctagattgta aaatgtattc taaaagtgtt ttaaaaatta aaaataaaaa   120
ccccccgaat aatgtgctgc gacgcaatta aaaaaaataa gaatcctgaa taatgtgctg   180
```

```
tgaagcagtt gaaagaaaat taaagaaccc aatataatat gctataaagc aatcaaaaaa      240
taatagtaag aaacccaaat aaaacccccgt tgaccatgtt cccaattaaa ttaacgcata      300
ttaatgcaaa aaatgcaata ttaagactag ttattaaacc gataattagt cttcaattat      360
taaaagatgt agttgatttg tattatcttt caattgctaa ttctaaatat attgga          416
```

<210> SEQ ID NO 38
<211> LENGTH: 31
<212> TYPE: DNA
<213> ORGANISM: Artificial Sequence
<220> FEATURE:
<223> OTHER INFORMATION: Description of Artificial Sequence: Forward
      primer

<400> SEQUENCE: 38

```
tcctgcagta cctttgagaa ccggttaatt c                                      31
```

<210> SEQ ID NO 39
<211> LENGTH: 33
<212> TYPE: DNA
<213> ORGANISM: Artificial Sequence
<220> FEATURE:
<223> OTHER INFORMATION: Description of Artificial Sequence: Reverse
      primer

<400> SEQUENCE: 39

```
ctggaattcc tttcatcatc tttttgaact ccc                                    33
```

<210> SEQ ID NO 40
<211> LENGTH: 538
<212> TYPE: DNA
<213> ORGANISM: Schizosaccharomyces pombe
<220> FEATURE:
<223> OTHER INFORMATION: ptr3 terminator

<400> SEQUENCE: 40

```
tacctttgag aaccggttaa ttcctggaat ttgcaacatt taatgccaat ggctctaata       60
aatttactaa attagtatta gcagtcttta aaaaacatta ataggcatgt atgaataatt      120
tattattttt cctatactct ttctaatttt tatgaactaa gatctgttat attttaaaaa      180 gtatttttgac atgtagtaaa attgttgttt ttttgagcaa ttttttttaac gtcggcgatt    240 ggcatttacg taagtttcga ctgctaacct cctaatttac ctaagagtat atctttactc      300
ggctacaaaa gtctatcgta tacattatat taaatttaac tagaattatt gccaatgtct      360
actgcctcaa aactttgtat cgtcggggcc ggtgtcttta gtgtttacat ggtttatttc      420
gtacataata atcagattat tgaacgagag gtaatattta cttatattaa agaaaatatg      480
caccatagct aatgtaagta tagaaaatgt cggcgggagt tcaaaagat gatgaaag         538
```

<210> SEQ ID NO 41
<211> LENGTH: 5998
<212> TYPE: DNA
<213> ORGANISM: Artificial Sequence
<220> FEATURE:
<223> OTHER INFORMATION: Description of Artificial Sequence: pSL12inv1t

<400> SEQUENCE: 41

```
gaatgtatat ataaaattaa taagctaagt gtaatactta aaaaatacat taattggaac       60
tcgtatccta ccattacaa tgttcatcca attttttcag attgtactgt aaatagcgtt       120
tgaaaacacc aaatttttaga agctaatcac tctcatcata atcgtctaca tcctcatcgt     180
```

```
tatcgacgat aaaagaatca tcttgcatgc tgggttcatc catgctatca aacgagggat    240
caacgtaaat aggtgttttc actgtagccg ctgctcttct ggttggcctc tttctaatcg    300
gagaatctga atcttctggt ggctctgcgt tagtcgaact agcttttgga gttgaactac    360
tacctggaat aataaaatca tcatcgtcat cttcaggtga ttgtttcttt accgagcttg    420
cttttttccc tttattcttc gcagaagcct tcgtggatgt tatggtggaa ggtttcaaac    480
tgctaggcaa caaatcatct tcatcgtctg aagaaaatat ggtagtagca actggtttat    540
tagtctttct tcctcttcca gacgccgagg ctgctatttt tttgacgggt tttttactac    600
ctgcgtcttc agagtcaaca gattgacttc ttttttcttga ttttccacta tcactgctat    660
ccaatcccgg gctcttagat atgcgatttt cttcaactga taagccatga gagttatcct    720
ctgtcttgac aatgtttatg tcagatgatt tctcaggttc tttcgacgct gcgaactcaa    780
gtaaagtttg ttgctttcga tttgttgtag atggtttgga ttcgctgcta gcttcttttt    840
taacagcagt acttgaggag gatccggcaa tagccctggg tttcctagta ccagtggatt    900
tacctcgagg cttcttttc gttcgattta caaaatctct tgaggattgc tcttcttcta    960
acatttctct ctgaatatca tccataacct tattccaagc atgctcaaat gcatccaaat   1020
catgaagcca caattcttta ggagtttttt taatcaaagc atccagttcg gccattactt   1080
cgtccttttt cttgagaagt tccacatacc gttcataggt caaagaccat aaaggcattg   1140
aaagaaggta attgtaggca tctgaatcct cgtcttgcga acatcacca gattgttctt   1200
cttcagcaag agcattttca acttctaaat caaccaaatg ccctttcttt ggtttactga   1260
taggttgaaa cttcttttcc ttcagctcca caatgagatc ctttttcttc ttttttgaaa   1320
ctacaagctc cccctctata atcatatgaa taaaccgcgc ttgatttgaa aatctatcaa   1380
accttttttc caattcatta accatatgct ctttacgtct ctggtatgtc cttaaacgta   1440
cttcgtaaaa ctcggtcaaa atatcttcaa cactgtcata cttcttgatc cgtccagatg   1500
catcaaaagc aatcatatta ctcgttgctt gagtacgcga cagtttaaac ttaacttcca   1560
aggattcatt taatgcttct ttcatgccag cttcggtaag cgtgacatta aagtgaacat   1620
ttccttcacc gtgatggctt tcatagtcca cgatgaattt acgaattttt tccgtaccaa   1680
caagaccagc ctccagatac tccttcattc gtacgattta aatgcggccg cttcggctgc   1740
ggcgagcggg tatcagctca ctcaaaggcg gtaatacggt tatccacaga atcaggggat   1800
aacgcaggaa agaacatgtg agcaaaaggc cagcaaaagg ccaggaaccg taaaaaggcc   1860
gcgttgctgg cgttttttcca taggctccgc ccccctgacg agcatcacaa aaatcgacgc   1920
tcaagtcaga ggtggcgaaa cccgacagga ctataaagat accaggcgtt ccccctgga   1980
agctccctcg tgcgctctcc tgttccgacc ctgccgctta ccggatacct gtccgccttt   2040
ctcccttcgg gaagcgtggc gctttctcaa tgctcacgct gtaggtatct cagttcggtg   2100
taggtcgttc gctccaagct gggctgtgtg cacgaacccc ccgttcagcc cgaccgctgc   2160
gccttatccg gtaactatcg tcttgagtcc aacccggtaa gacacgactt atcgccactg   2220
gcagcagcca ctggtaacag gattagcaga gcgaggtatg taggcggtgc tacagagttc   2280
ttgaagtggt ggcctaacta cggctacact agaaggacag tatttggtat ctgcgctctg   2340
ctgaagccag ttaccttcgg aaaaagagtt ggtagctctt gatccggcaa caaaccacc   2400
gctggtagcg gtggtttttt tgtttgcaag cagcagatta cgcgcagaaa aaaaggatct   2460
caagaagatc ctttgatctt ttctacgggg tctgacgctc agtggaacga aaactcacgt   2520
taagggattt tggtcatgag cttgcgccgt cccgtcaagt cagcgtaatg ctctgccagt   2580
```

-continued

```
gttacaacca attaaccaat tctgattaga aaaactcatc gagcatcaaa tgaaactgca      2640
atttattcat atcaggatta tcaataccat attttgaaa aagccgtttc tgtaatgaag       2700
gagaaaactc accgaggcag ttccatagga tggcaagatc ctggtatcgg tctgcgattc     2760
cgactcgtcc aacatcaata caacctatta atttcccctc gtcaaaaata aggttatcaa     2820
gtgagaaatc accatgagtg acgactgaat ccggtgagaa tggcaagagc ttatgcattt     2880
ctttccagac ttgttcaaca ggccagccat tacgctcgtc atcaaaatca ctcgcatcaa     2940
ccaaaccgtt attcattcgt gattgcgcct gagcgaggcg aaatacgcga tcgctgttaa     3000
aaggacaatt acaaacagga atcgaatgca accggcgcag gaacactgcc agcgcatcaa    3060
caatattttc acctgaatca ggatattctt ctaatacctg gaatgctgtt ttcccaggga    3120
tcgcagtggt gagtaaccat gcatcatcag gagtacggat aaaatgcttg atggtcggaa    3180
gaggcataaa ttccgtcagc cagtttagtc tgaccatctc atctgtaaca tcattggcaa    3240
cgctaccttt gccatgtttc agaaacaact ctggcgcatc gggcttccca tacaatcggt    3300
agattgtcgc acctgattgc ccgacattat cgcgagccca tttataccca tataaatcag    3360
catccatgtt ggaatttaat cgcggcctcg tcgagcaaga cgtttcccgt tgaatatggc    3420
tcataacacc ccttgtatta ctgtttatgt aagcagacag ttttattgtt catttaaatg    3480
cggccgcgta cggcggcttc gatagcttca gcctccttag gagcattcaa accataacga    3540
aggagaaggg aagcagataa aattgtacca acaggattaa caatgcccctt gccagcgata    3600 tcgggagcgc taccgtgaat gggctcaacc aaacaatgaa cctttcttc tgattttcct     3660 accacaccgg aaagggaggc agaaggcaaa aggcccaagc taccaggaat gacagaagcc    3720
tcatctgaaa taatgtcacc aaacaagttg tcagtcaaaa caacaccgtt aagtgtacga    3780
gggctcttga ccaaaagcat ggctgcggag tcaatgagct ggttttttaa ggtaaggtga    3840
ggatattcct ccttaaaaat cttagctaca gtcttgcgcc aaagacgaga agttgccaaa    3900
acattagctt tgtcgagtaa tgtgacggga gcaggagggt tggaagttc agctaaccaa    3960 gcagccaaac gagcaatacg agaaacttct tccaaactgt aaggccaagt gtccatagca    4020
taacccgatc cgttgtcctc agtgcgctca ccaaagtaac aacctccagt aagttctcgt    4080
acaacacaaa aatcgacacc ttcaacgatt tcaggcttca aagggctgta cttgactaaa    4140
gacttgctgg caaagttgca aggtcgaagg ttggcccaaa cacccatact cttacgaagc    4200
ttcaataaac cttgctcagg acgacaattg gggttggtcc attcaggacc accaacggca    4260
cccaaaagaa caccgtcagc ttccaaacaa gccttcacag tctcgtcagt caagggggtt    4320
ccataggcat caatagaggc acctccaatc ttgtgttctt caaactcgag ttttaactca    4380
ggtcgcttct tctcaacgac tttcaaaacc tccaaggcag aagcaacaat ttcagggcca    4440
atatggtctc ctggtaagac gacgattttc tttgcacaca tgttgttgaa gaagttttgt    4500
tgtgaaatgg tttcgtgaaa gtttcagacc ctaccgcaaa aatgcctggt tcgggaaac     4560 tcaacactgt tgcactttt atactacaga ttgggatatc gataatattg cgtaaaaaat     4620
ccttttttta aaaagcttgt ttacagtaac gtaaatgacc agaaatcaga tgaaaatcac    4680
aagaaagcaa ataattcacg ttaaatcctg atatgtttga ttttgtgatg aaatcatgga    4740
tgttcatagg aattgttgaa attgcgcttt tttaacgaaa tatacaagta tcctggagct    4800
tacttaatta attaatgaat ctttgttcct aggggcttca actagctcgg gatgatatcc    4860
catattttat gcccgacacc gtttgtcatc cgcttagtcg tgataccgt ctgccacata     4920
```

```
gcgaatgtca aaggattatg ctactttacg tgagaatgaa atatagactt tacacatcgc    4980
cacatgatgg catcgataga gctgctagtt tcaattactt tcaattaacg agtgaaaagc    5040
ggatgtaccg catcatctgt tgagcgaaat agtctacgta aaatcaaatg gctaatttg     5100 tcgctgaatt aacccaaaag caaaaatacg attgcaattc tcattacgaa atgctgaatg    5160
ggatggaaaa taaattgatg tcacaatttc cgaggactct tacaaatatt atatatagag    5220
cacggggtac atcactatcg attcgaattt tcaagaagta atatttcgca ccgtagtact    5280
ttttgtaagc cgttttatta aatcagaaag aactccaatt ttatttataa acaatgtgaa    5340
gcaggtgtcg gtacccgggg atcctctaga gtcgacctgc aggcatgcaa gcttatattt    5400
tgtttcaagt taggaaagta taataacttt tgtccctgca tattcaattg taaagtttag    5460
tttatccttt catcgtaacc acaattgtca cctaaatctc taaaaatctc ttcacttatc    5520
tagttaatgt cgtaacaaaa aagtccagta gcttcgggaa atgatgcttg gaatcataca    5580
agtcgacgtg ggttttccct tcaacaatgt acagctcttt tggctcggaa gcgacagcat    5640
atgcttcctt tgaaaaatac agagtgtcag ccttctcacc agctatgtac aacaaaggcc    5700
taggagccat ttgtttaaga acatccgtgg ctccataaaa gccagccaat aactccatgc    5760
tccacggctg gaaaataccg gtggatcgag gatgggaacc acgcggtgta caataatagt    5820
cataggcttc tttgaataat aatgggggtgg catcagacaa ttgctctctt tgggggaata   5880
aattgaacaa gtcatatgac tcacccttac aaatttggtt cgcgaggcag cggcaccttc    5940
tagtaggcac tagtgaattc gagtatgtgt acgagttgtc tttaaaccca cagaggta     5998
```

<210> SEQ ID NO 42
<211> LENGTH: 6057
<212> TYPE: DNA
<213> ORGANISM: Artificial Sequence
<220> FEATURE:
<223> OTHER INFORMATION: Description of Artificial Sequence: pSL12ihc2t

<400> SEQUENCE: 42

```
gaatgtatat ataaaattaa taagctaagt gtaatactta aaaatacat taattggaac      60 tcgtatccta ccatttacaa tgttcatcca atttttcag attgtactgt aaatagcgtt     120
tgaaaacacc aaattttaga agctaatcac tctcatcata atcgtctaca tcctcatcgt    180
tatcgacgat aaaagaatca tcttgcatgc tgggttcatc catgctatca aacgagggat    240
caacgtaaat aggtgttttc actgtagccg ctgctcttct ggttggcctc tttctaatcg    300
gagaatctga atcttctggt ggctctgcgt tagtcgaact agcttttgga gttgaactac    360
tacctggaat aataaaatca tcatcgtcat cttcaggtga ttgtttcttt accgagcttg    420
ctttttttcc tttattcttc gcagaagcct tcgtggatgt tatggtggaa ggtttcaaac    480
tgctaggcaa caaatcatct tcatcgtctg aagaaaatat ggtagtagca actggtttat    540 tagtcttttct tcctcttcca gacgccgagg ctgctatttt tttgacgggt ttttactac    600 ctgcgtcttc agagtcaaca gattgacttc ttttttcttga tttttccacta tcactgctat    660 ccaatcccgg gctcttagat atgcgatttt cttcaactga taagccatga gagttatcct    720
ctgtcttgac aatgttatg tcagatgatt tctcaggttc tttcgacgct gcgaactcaa      780
gtaaagtttg ttgctttcga tttgttgtag atggtttgga ttcgctgcta gcttctttt    840 taacagcagt acttgaggag gatccggcaa tagccctggg tttcctagta ccagtggatt    900
tacctcgagg cttctttttc gttcgattta caaaatctct tgaggattgc tcttcttcta    960
acatttctct ctgaatatca tccataaccct tattccaagc atgctcaaat gcatccaaat   1020
```

```
catgaagcca caattcttta ggagttttt taatcaaagc atccagttcg gccattactt    1080
cgtccttttt cttgagaagt tccacatacc gttcataggt caaagaccat aaaggcattg    1140
aaagaaggta attgtaggca tctgaatcct cgtcttgcga acatcacca gattgttctt    1200 cttcagcaag agcattttca acttctaaat caaccaaatg ccctttcttt ggtttactga    1260
taggttgaaa cttcttttcc ttcagctcca caatgagatc ctttttcttc ttttttgaaa    1320
ctacaagctc cccctctata atcatatgaa taaaccgcgc ttgatttgaa aatctatcaa    1380 acctttttc caattcatta accatatgct ctttacgtct ctggtatgtc cttaaacgta     1440
cttcgtaaaa ctcggtcaaa atatcttcaa cactgtcata cttcttgatc cgtccagatg    1500
catcaaaagc aatcatatta ctcgttgctt gagtacgcga cagtttaaac ttaacttcca    1560
aggattcatt taatgcttct ttcatgccag cttcggtaag cgtgacatta aagtgaacat    1620
ttccttcacc gtgatggctt tcatagtcca cgatgaattt acgaatttt tccgtaccaa     1680 caagaccagc ctccagatac tccttcattc gtacgattta aatgcggccg cttcggctgc    1740
ggcgagcggg tatcagctca ctcaaaggcg gtaatacggt tatccacaga atcaggggat    1800
aacgcaggaa agaacatgtg agcaaaaggc cagcaaaagg ccaggaaccg taaaaaggcc    1860
gcgttgctgg cgttttttcca taggctccgc cccctgacg agcatcacaa aaatcgacgc    1920
tcaagtcaga ggtggcgaaa cccgacagga ctataaagat accaggcgtt ccccctggaa    1980
agctccctcg tgcgctctcc tgttccgacc ctgccgctta ccggatacct gtccgccttt    2040
ctcccttcgg gaagcgtggc gctttctcaa tgctcacgct gtaggtatct cagttcggtg    2100
taggtcgttc gctccaagct gggctgtgtg cacgaacccc ccgttcagcc cgaccgctgc    2160
gccttatccg gtaactatcg tcttgagtcc aacccggtaa gacacgactt atcgccactg    2220
gcagcagcca ctggtaacag gattagcaga gcgaggtatg taggcggtgc tacagagttc    2280
ttgaagtggt ggcctaacta cggctacact agaaggacag tatttggtat ctgcgctctg    2340
ctgaagccag ttaccttcgg aaaaagagtt ggtagctctt gatccggcaa acaaaccacc    2400
gctggtagcg gtggttttt tgtttgcaag cagcagatta cgcgcagaaa aaaggatct     2460 caagaagatc ctttgatctt ttctacgggg tctgacgctc agtggaacga aaactcacgt    2520
taagggattt tggtcatgag cttgcgccgt cccgtcaagt cagcgtaatg ctctgccagt    2580
gttacaacca attaaccaat tctgattaga aaaactcatc gagcatcaaa tgaaactgca    2640
atttattcat atcaggatta tcaataccat attttgaaa aagccgtttc tgtaatgaag     2700
gagaaaactc accgaggcag ttccatagga tggcaagatc ctggtatcgg tctgcgattc    2760
cgactcgtcc aacatcaata caacctatta atttcccctc gtcaaaaata aggttatcaa    2820
gtgagaaatc accatgagtg acgactgaat ccggtgagaa tggcaagagc ttatgcattt    2880
ctttccagac ttgttcaaca ggccagccat tacgctcgtc atcaaaatca ctcgcatcaa    2940
ccaaaccgtt attcattcgt gattgcgcct gagcgaggcg aaatacgcga tcgctgttaa    3000
aaggacaatt acaaacagga atcgaatgca accggcgcag gaacactgcc agcgcatcaa    3060
caatattttc acctgaatca ggatattctt ctaatacctg gaatgctgtt ttcccaggga    3120
tcgcagtggt gagtaaccat gcatcatcag gagtacggat aaaatgcttg atggtcgaa    3180 gaggcataaa ttccgtcagc cagtttagtc tgaccatctc atctgtaaca tcattggcaa    3240
cgctaccttt gccatgtttc agaaacaact ctggcgcatc gggcttccca tacaatcggt    3300
agattgtcgc acctgattgc ccgacattat cgcgagccca tttataccca tataaatcag    3360
```

```
catccatgtt ggaatttaat cgcggcctcg tcgagcaaga cgtttcccgt tgaatatggc      3420
tcataacacc ccttgtatta ctgtttatgt aagcagacag ttttattgtt catttaaatg      3480
cggccgcgta cggcggcttc gatagcttca gcctccttag gagcattcaa accataacga      3540
aggagaaggg aagcagataa aattgtacca acaggattaa caatgcccct gccagcgata      3600
tcgggagcgc taccgtgaat gggctcaacc aaacaatgaa cctttcttc tgattttcct       3660 accacaccgg aaagggaggc agaaggcaaa aggcccaagc taccaggaat gacagaagcc      3720
tcatctgaaa taatgtcacc aaacaagttg tcagtcaaaa caacaccgtt aagtgtacga      3780
gggctcttga ccaaaagcat ggctgcggag tcaatgagct ggttttttaa ggtaaggtga      3840
ggatattcct ccttaaaaat cttagctaca gtcttgcgcc aaagacgaga agttgccaaa      3900
acattagctt tgtcgagtaa tgtgacggga gcaggagggt tggaagtttc agctaaccaa      3960
gcagccaaac gagcaatacg agaaacttct tccaaactgt aaggccaagt gtccatagca      4020
taacccgatc cgttgtcctc agtgcgctca ccaaagtaac aacctccagt aagttctcgt      4080
acaacacaaa aatcgacacc ttcaacgatt tcaggcttca aagggctgta cttgactaaa      4140
gacttgctgg caaagttgca aggtcgaagg ttggcccaaa cacccatact cttacgaagc      4200
ttcaataaac cttgctcagg acgacaattg gggttggtcc attcaggacc accaacggca      4260
cccaaaagaa caccgtcagc ttccaaacaa gccttcacag tctcgtcagt caaggggtt       4320 ccataggcat caatagaggc acctccaatc ttgtgttctt caaactcgag ttttaactca      4380
ggtcgcttct tctcaacgac tttcaaaacc tccaaggcag aagcaacaat tcagggcca       4440 atatggtctc ctggtaagac gacgattttc tttgcacaca tgttgttgaa gaagttttgt      4500
tgtgaaatgg tttcgtgaaa gtttcagacc ctaccgcaaa aatgcctggt tcgggaaac      4560 tcaacactgt tgcactttt atactacaga ttgggatatc gataatattg cgtaaaaaat       4620
ccttttttta aaaagcttgt ttacagtaac gtaaatgacc agaaatcaga tgaaaatcac      4680
aagaaagcaa ataattcacg ttaaatcctg atatgtttga ttttgtgatg aaatcatgga      4740
tgttcatagg aattgttgaa attgcgcttt tttaacgaaa tatacaagta tcctggagct      4800
tacttaatta attaatgaat cttttgttcct aggggcttca actagctcgg gatgatatcc      4860
catattttat gcccgacacc gtttgtcatc cgcttagtcg tgatacccgt ctgccacata      4920
gcgaatgtca aaggattatg ctactttacg tgagaatgaa atatagactt tacacatcgc      4980
cacatgatgg catcgataga gctgctagtt tcaattactt tcaattaacg agtgaaaagc      5040
ggatgtaccg catcatctgt tgagcgaaat agtctacgta aaatcaaatg ggctaatttg      5100
tcgctgaatt aacccaaaag caaaaatacg attgcaattc tcattacgaa atgctgaatg      5160
ggatggaaaa taaattgatg tcacaatttc cgaggactct tacaaatatt atatatagag      5220
cacggggtac atcactatcg attcgaattt tcaagaagta atatttcgca ccgtagtact      5280
ttttgtaagc cgttttatta aatcagaaag aactccaatt ttatttataa acaatgtgaa      5340
gcaggtgtcg gtacccgggg atcctctaga gtcgacctgc agaataaagc aacgaactaa      5400
acgaaattta ttgcttctaa ctttaacttt ttggcaagct atgatgttca caagctgtca      5460
tagcttattt tacgatttca cccttatata tttttaatga gatttcaatc acattaaaat      5520
acatgtcttt attttttatag gcagtttgtt catgcatata tgtagttttg tatttccttc      5580
gaacagcctt aattgatgta gcagttactt tttaatggaa ttgtgtagtt gccttgttaa      5640
tttctcatta cgacaaggtt gtgttgtgta aatactcttt tctttagtaa acaatacgcg      5700
tcatactaag ggtaagtacc attattatgg tgtatcactt gtaactttca gtacagctaa      5760
```

```
ttcttcacat ttaccaatag caaaccggtc taaaaaacat ctattatgac aataaaaagc    5820
tccgaacttc tgaaaagaat gactgcatat gaatgtgaaa ttaaaaaaaa tatcaacact    5880
acttcttaat gaatgtatta ctttggttct aggaaaatca aaatgatata gtattacaaa    5940
ttaatcaata tattattcag tgttgttttt gcatgttaat atctccctaa gtggttacaa    6000
tctattcact agtgaattcg agtatgtgta cgagttgtct ttaaacccac agaggta       6057

<210> SEQ ID NO 43
<211> LENGTH: 33
<212> TYPE: DNA
<213> ORGANISM: Artificial Sequence
<220> FEATURE:
<223> OTHER INFORMATION: Description of Artificial Sequence: Reverse
      primer

<400> SEQUENCE: 43
ggactagtga atagattgta accacttagg gag                                 33

<210> SEQ ID NO 44
<211> LENGTH: 5778
<212> TYPE: DNA
<213> ORGANISM: Artificial Sequence
<220> FEATURE:
<223> OTHER INFORMATION: Description of Artificial Sequence: pSL14LPIt

<400> SEQUENCE: 44
actagtgaat tcgagtatgt gtacgagttg tctttaaacc cacagaggta gaatgtatat    60
ataaaattaa taagctaagt gtaatactta aaaaatacat taattggaac tcgtatccta    120
ccatttacaa tgttcatcca atttttcag attgtactgt aaatagcgtt tgaaaacacc    180
aaattttaga agctaatcac tctcatcata atcgtctaca tcctcatcgt tatcgacgat    240
aaaagaatca tcttgcatgc tgggttcatc catgctatca aacgagggat caacgtaaat    300
aggtgttttc actgtagccg ctgctcttct ggttggcctc tttctaatcg agaatctga    360 atcttctggt ggctctgcgt tagtcgaact agcttttgga gttgaactac tacctggaat    420
aataaaatca tcatcgtcat cttcaggtga ttgtttcttt accgagcttg ctttttccc    480 tttattcttc gcagaagcct tcgtggatgt tatggtggaa ggtttcaaac tgctaggcaa    540
caaatcatct tcatcgtctg aagaaaatat ggtagtagca actggtttat tagtcttttct    600 tcctcttcca gacgccgagg ctgctatttt tttgacgggt ttttactac ctgcgtcttc    660 agagtcaaca gattgacttc ttttttcttga ttttccacta tcactgctat ccaatcccgg    720
gctcttagat atgcgatttt cttcaactga taagccatga gagttatcct ctgtcttgac    780
aatgtttatg tcagatgatt tctcaggttc tttcgacgct gcgaactcaa gtaaagtttg    840
ttgctttcga tttgttgtag atggtttgga ttcgctgcta gcttcttttt taacagcagt    900
acttgaggag gatccggcaa tagccctggg tttcctagta ccagtggatt tacctcgagg    960 cttcttttc gttcgattta caaaatctct tgaggattgc tcttcttcta acatttctct    1020
ctgaatatca tccataacct tattccaagc atgctcaaat gcatccaaat catgaagcca    1080
caattcttta ggagtttttt taatcaaagc atccagttcg ccattactt cgtccttttt    1140 cttgagaagt tccacatacc gttcataggt caaagaccat aaaggcattg aagaaggta    1200 attgtaggca tctgaatcct cgtcttgcga aacatcacca gattgttctt cttcagcaag    1260
agcattttca acttctaaat caaccaaatg ccctttcttt ggtttactga taggttgaaa    1320 cttctttttcc ttcagctcca caatgagatc cttttttcttc ttttttgaaa ctacaagctc    1380
```

```
cccctctata atcatatgaa taaaccgcgc ttgatttgaa aatctatcaa acctttttc    1440
caattcatta accatatgct ctttacgtct ctggtatgtc cttaaacgta cttcgtaaaa   1500
ctcggtcaaa atatcttcaa cactgtcata cttcttgatc cgtccagatg catcaaaagc   1560
aatcatatta ctcgttgctt gagtacgcga cagtttaaac ttaacttcca aggattcatt   1620
taatgcttct ttcatgccag cttcggtaag cgtgacatta aagtgaacat ttccttcacc   1680
gtgatggctt tcatagtcca cgatgaattt acgaattttt tccgtaccaa caagaccagc   1740
ctccagatac tccttcattc gtacgattta aatgcggccg cttcggctgc ggcgagcggg   1800
tatcagctca ctcaaaggcg gtaatacggt tatccacaga atcaggggat aacgcaggaa   1860
agaacatgtg agcaaaaggc cagcaaaagg ccaggaaccg taaaaaggcc gcgttgctgg   1920
cgttttccca taggctccgc cccctgacg agcatcacaa aaatcgacgc tcaagtcaga    1980
ggtggcgaaa cccgacagga ctataaagat accaggcgtt tccccctgga agctccctcg   2040
tgcgctctcc tgttccgacc ctgccgctta ccggatacct gtccgccttt ctcccttcgg   2100
gaagcgtggc gctttctcaa tgctcacgct gtaggtatct cagttcggtg taggtcgttc   2160
gctccaagct gggctgtgtg cacgaacccc ccgttcagcc cgaccgctgc gccttatccg   2220
gtaactatcg tcttgagtcc aacccggtaa gacacgactt atcgccactg gcagcagcca   2280
ctggtaacag gattagcaga gcgaggtatg taggcggtgc tacagagttc ttgaagtggt   2340
ggcctaacta cggctacact agaaggacag tatttggtat ctgcgctctg ctgaagccag   2400
ttaccttcgg aaaaagagtt ggtagctctt gatccggcaa acaaaccacc gctggtagcg   2460
gtggtttttt tgtttgcaag cagcagatta cgcgcagaaa aaaaggatct caagaagatc   2520
ctttgatctt ttctacgggg tctgacgctc agtggaacga aaactcacgt taagggattt   2580
tggtcatgag cttgcgccgt cccgtcaagt cagcgtaatg ctctgccagt gttacaacca   2640
attaaccaat tctgattaga aaaactcatc gagcatcaaa tgaaactgca atttattcat   2700
atcaggatta tcaataccat attttttgaaa aagccgtttc tgtaatgaag gagaaaactc   2760
accgaggcag ttccatagga tggcaagatc ctggtatcgg tctgcgattc cgactcgtcc   2820
aacatcaata caacctatta atttcccctc gtcaaaaata aggttatcaa gtgagaaatc   2880
accatgagtg acgactgaat ccggtgagaa tggcaagagc ttatgcattt ctttccagac   2940
ttgttcaaca ggccagccat tacgctcgtc atcaaaatca ctcgcatcaa ccaaaccgtt   3000
attcattcgt gattgcgcct gagcgaggcg aaatacgcga tcgctgttaa aaggacaatt   3060
acaaacagga atcgaatgca accggcgcag gaacactgcc agcgcatcaa caatatttc    3120
acctgaatca ggatattctt ctaatacctg gaatgctgtt ttcccaggga tcgcagtggt   3180
gagtaaccat gcatcatcag gagtacggat aaaatgcttg atggtcggaa gaggcataaa   3240
ttccgtcagc cagtttagtc tgaccatctc atctgtaaca tcattggcaa cgctaccttt   3300
gccatgtttc agaaacaact ctggcgcatc gggcttccca tacaatcggt agattgtcgc   3360
acctgattgc ccgacattat cgcgagccca tttatacccca tataaatcag catccatgtt   3420
ggaatttaat cgcggcctcg tcagcaaga cgtttcccgt tgaatatggc tcataacacc    3480
ccttgtatta ctgtttatgt aagcagacag ttttattgtt catttaaatg cggcgcgta    3540
cggcggcttc gatagcttca gcctccttag gagcattcaa accataacga aggagaaggg   3600
aagcagataa aattgtacca acaggattaa caatgccctt gccagcgata tcgggagcgc   3660
taccgtgaat gggctcaacc aaacaatgaa ccttttcttc tgattttcct accacaccgg   3720
```

```
aaagggaggc agaaggcaaa aggcccaagc taccaggaat gacagaagcc tcatctgaaa    3780
taatgtcacc aaacaagttg tcagtcaaaa caacaccgtt aagtgtacga gggctcttga    3840
ccaaaagcat ggctgcggag tcaatgagct ggttttttaa ggtaaggtga ggatattcct    3900
ccttaaaaat cttagctaca gtcttgcgcc aaagacgaga agttgccaaa acattagctt    3960
tgtcgagtaa tgtgacggga gcaggagggt tggaagtttc agctaaccaa gcagccaaac    4020
gagcaatacg agaaacttct tccaaactgt aaggccaagt gtccatagca taacccgatc    4080
cgttgtcctc agtgcgctca ccaaagtaac aacctccagt aagttctcgt acaacacaaa    4140
aatcgacacc ttcaacgatt tcaggcttca aagggctgta cttgactaaa gacttgctgg    4200
caaagttgca aggtcgaagg ttggcccaaa cacccatact cttacgaagc ttcaataaac    4260
cttgctcagg acgacaattg gggttggtcc attcaggacc accaacggca cccaaaagaa    4320
caccgtcagc ttccaaacaa gccttcacag tctcgtcagt caaaggggtt ccataggcat    4380
caatagaggc acctccaatc ttgtgttctt caaactcgag ttttaactca ggtcgcttct    4440
tctcaacgac tttcaaaacc tccaaggcag aagcaacaat ttcagggcca atatggtctc    4500
ctggtaagac gacgattttc tttgcacaca tgttgttgaa gaagttttgt tgtgaaatgg    4560
tttcgtgaaa gtttcagacc ctaccgcaaa atgcctggt ttcgggaaac tcaacactgt    4620
tgcacttttt atactacaga ttgggatatc gataatattg cgtaaaaaat ccttttttta    4680
aaaagcttgt ttacagtaac gtaaatgacc agaaatcaga tgaaaatcac aagaaagcaa    4740
ataattcacg ttaaatcctg atatgtttga ttttgtgatg aaatcatgga tgttcatagg    4800
aattgttgaa attgcgcttt tttaacgaaa tatacaagta tcctggagct tacttaatta    4860
attaatgaat ctttgtttct agttttaccc atcgtaaaga tcttgagagc tctccacttt    4920
gaacctctaa cctagcgagg gttttaccgt actcgctatc tcgctttgca aatccacaaa    4980
gcttctgtat tacatcataa gaaagtagag tgggcgctca ttggaaatag cttacgtagc    5040
tcagaaaacg aatggtgcga agaaaagggg ctttgctaga agctgctcat tatttgtctg    5100
attggatagc gagctatctg atagaaaact acgtaattcc ttggatcgca gttttctcca    5160
gtttctaatg ctaactgacg caaatgtgat gtaatgggct gcgatcataa tgacatgagc    5220
aattggacaa gaagctataa atacgagtcc aagttcaaca gtttaatcat tcaattcaat    5280
tccaatcaat ttaattgtct taaatattca aaacatgtga agcaggtgtc ggtacccggg    5340
gatcctctag agtcgacctg caggcatgca agcttaaata ggaaagtttc ttcaacagga    5400
ttacagtgta gctacctaca tgctgaaaaa tatagccttt aaatcatttt tatattataa    5460
ctctgtataa tagagataag tccatttttt aaaaatgttt tccccaaacc ataaaaccct    5520
atacaagttg ttctagtaac aatacatgag aaagatgtct atgtagctga aaataaaatg    5580
acgtcacaag acgatctgcc tcgcgcgttt cggtgatgac ggtgaaaacc tctgacacat    5640
gcagctcccg gagacggtca cagcttgtct gtaagcggat gccggagca gacaagcccg    5700 tcagggcgcg tcagcgggtg ttggcgggtg tcggggcgca gccatgaccc agtcacgtag    5760
cgatagcgga gcccgggc                                                 5778

<210> SEQ ID NO 45
<211> LENGTH: 5988
<212> TYPE: DNA
<213> ORGANISM: Artificial Sequence
<220> FEATURE:
<223> OTHER INFORMATION: Description of Artificial Sequence: pSL14ihc2t

<400> SEQUENCE: 45
```

```
gaattcgagt atgtgtacga gttgtctttt aacccacaga ggtagaatgt atatataaaa      60
ttaataagct aagtgtaata cttaaaaaat acattaattg gaactcgtat cctaccattt     120
acaatgttca tccaattttt tcagattgta ctgtaaatag cgtttgaaaa caccaaattt     180
tagaagctaa tcactctcat cataatcgtc tacatcctca tcgttatcga cgataaaaga     240
atcatcttgc atgctgggtt catccatgct atcaaacgag ggatcaacgt aaataggtgt     300
tttcactgta gccgctgctc ttctggttgg cctctttcta atcggagaat ctgaatcttc     360
tggtggctct gcgttagtcg aactagcttt tggagttgaa ctactacctg aataataaa      420
atcatcatcg tcatcttcag gtgattgttt ctttaccgag cttgcttttt tccctttatt     480
cttcgcagaa gccttcgtgg atgttatggt ggaaggtttc aaactgctag caacaaatc      540
atcttcatcg tctgaagaaa atatggtagt agcaactggt ttattagtct tcttcctct      600
tccagacgcc gaggctgcta ttttttttgac gggttttttta ctacctgcgt cttcagagtc   660
aacagattga cttcttttttc ttgattttcc actatcactg ctatccaatc ccgggctctt   720
agatatgcga ttttcttcaa ctgataagcc atgagagtta tcctctgtct tgacaatgtt    780
tatgtcagat gatttctcag gttctttcga cgctgcgaac tcaagtaaag tttgttgctt    840
tcgatttgtt gtagatggtt tggattcgct gctagcttct tttttaacag cagtacttga    900
ggaggatccg gcaatagccc tgggtttcct agtaccagtg gatttacctc gaggcttctt    960
tttcgttcga tttacaaaat ctcttgagga ttgctcttct tctaacattt ctctctgaat   1020
atcatccata accttattcc aagcatgctc aaatgcatcc aaatcatgaa gccacaattc   1080
tttaggagtt tttttaatca agcatccag ttcggccatt acttcgtcct tttctcttgag    1140
aagttccaca taccgttcat aggtcaaaga ccataaaggc attgaaagaa ggtaattgta   1200
ggcatctgaa tcctcgtctt gcgaaacatc accagattgt tcttcttcag caagagcatt   1260
ttcaacttct aaatcaacca aatgcccttt ctttggttta ctgataggtt gaaacttctt   1320
ttccttcagc tccacaatga gatcctttttt cttctttttt gaaactacaa gctccccctc   1380
tataatcata tgaataaacc gcgcttgatt tgaaaatcta tcaaaccttt tttccaattc   1440
attaaccata tgctctttac gtctctggta tgtccttaaa cgtacttcgt aaaactcggt   1500
caaaatatct tcaacactgt catacttctt gatccgtcca gatgcatcaa aagcaatcat   1560
attactcgtt gcttgagtac gcgacagttt aaacttaact tccaaggatt catttaatgc   1620
ttctttcatg ccagcttcgg taagcgtgac attaaagtga acatttcctt caccgtgatg   1680
gctttcatag tccacgatga atttacgaat tttttccgta ccaacaagac cagcctccag   1740
atactccttc attcgtacga tttaaatgcg ccgcttcgg ctgcggcgag cgggtatcag    1800
ctcactcaaa ggcggtaata cggttatcca cagaatcagg gataacgca ggaaagaaca    1860
tgtgagcaaa aggccagcaa aaggccagga accgtaaaaa ggccgcgttg ctggcgtttt   1920
tccataggct ccgcccccct gacgagcatc acaaaaatcg acgctcaagt cagaggtggc   1980
gaaacccgac aggactataa agataccagg cgtttccccc tggaagctcc ctcgtgcgct   2040
ctcctgttcc gaccctgccg cttaccggat acctgtccgc ctttctccct tcgggaagcg   2100
tggcgctttc tcaatgctca cgctgtaggt atctcagttc ggtgtaggtc gttcgctcca   2160
agctgggctg tgtgcacgaa ccccccgttc agcccgaccg ctgcgcctta ccggtaact    2220
atcgtcttga gtccaacccg gtaagacacg acttatcgcc actggcagca gccactggta   2280
acaggattag cagagcgagg tatgtaggcg gtgctacaga gttcttgaag tggtggccta   2340
```

```
actacggcta cactagaagg acagtatttg gtatctgcgc tctgctgaag ccagttacct    2400
tcggaaaaag agttggtagc tcttgatccg gcaaacaaac caccgctggt agcggtggtt    2460
tttttgtttg caagcagcag attacgcgca gaaaaaagg atctcaagaa gatcctttga     2520
tcttttctac ggggtctgac gctcagtgga acgaaaactc acgttaaggg attttggtca    2580
tgagcttgcg ccgtcccgtc aagtcagcgt aatgctctgc cagtgttaca accaattaac    2640
caattctgat tagaaaaact catcgagcat caaatgaaac tgcaatttat tcatatcagg    2700
attatcaata ccatattttt gaaaaagccg tttctgtaat gaaggagaaa actcaccgag    2760
gcagttccat aggatggcaa gatcctggta tcggtctgcg attccgactc gtccaacatc    2820
aatacaacct attaatttcc cctcgtcaaa aataaggtta tcaagtgaga atcaccatg     2880 agtgacgact gaatccggtg agaatggcaa gagcttatgc atttctttcc agacttgttc    2940
aacaggccag ccattacgct cgtcatcaaa atcactcgca tcaaccaaac cgttattcat    3000
tcgtgattgc gcctgagcga ggcgaaatac gcgatcgctg ttaaaaggac aattacaaac    3060
aggaatcgaa tgcaaccggc gcaggaacac tgccagcgca tcaacaatat tttcacctga    3120
atcaggatat tcttctaata cctggaatgc tgttttccca gggatcgcag tggtgagtaa    3180
ccatgcatca tcaggagtac ggataaaatg cttgatggtc ggaagaggca taaattccgt    3240
cagccagttt agtctgacca tctcatctgt aacatcattg gcaacgctac ctttgccatg    3300
tttcagaaac aactctggcg catcgggctt cccatacaat cggtagattg tcgcacctga    3360
ttgcccgaca ttatcgcgag cccatttata cccatataaa tcagcatcca tgttggaatt    3420
taatcgcggc ctcgtcgagc aagacgtttc ccgttgaata tggctcataa cacccccttgt    3480 attactgttt atgtaagcag acagttttat tgttcattta aatgcggccg cgtacggcgg    3540
cttcgatagc ttcagcctcc ttaggagcat tcaaaccata acgaaggaga agggaagcag    3600
ataaaattgt accaacagga ttaacaatgc ccttgccagc gatatcggga gcgctaccgt    3660
gaatgggctc aaccaaacaa tgaaccttt cttctgattt tcctaccaca ccggaaaggg     3720
aggcagaagg caaaaggccc aagctaccag gaatgacaga agcctcatct gaaataatgt    3780
caccaaacaa gttgtcagtc aaaacaacac cgttaagtgt acgagggctc ttgaccaaaa    3840
gcatggctgc ggagtcaatg agctggtttt ttaaggtaag gtgaggatat tcctccttaa    3900
aaatcttagc tacagtcttg cgccaaagac gagaagttgc caaaacatta gctttgtcga    3960
gtaatgtgac gggagcagga gggttggaag tttcagctaa ccaagcagcc aaacgagcaa    4020
tacgagaaac ttcttccaaa ctgtaaggcc aagtgtccat agcataaccc gatccgttgt    4080
cctcagtgcg ctcaccaaag taacaacctc cagtaagttc tcgtacaaca caaaaatcga    4140
caccttcaac gatttcaggc ttcaaagggc tgtacttgac taaagacttg ctggcaaagt    4200
tgcaaggtcg aaggttggcc caaacaccca tactcttacg aagcttcaat aaaccttgct    4260
caggacgaca attgggggttg gtccattcag gaccaccaac ggcacccaaa gaacaccgt    4320 cagcttccaa acaagccttc acagtctcgt cagtcaaagg ggttccatag gcatcaatag    4380
aggcacctcc aatcttgtgt tcttcaaact cgagttttaa ctcaggtcgc ttcttctcaa    4440
cgactttcaa aacctccaag gcagaagcaa caatttcagg gccaatatgg tctcctggta    4500
agacgacgat tttctttgca cacatgttgt tgaagaagtt ttgttgtgaa atggtttcgt    4560
gaaagtttca gaccctaccg caaaaatgcc tggtttcggg aaactcaaca ctgttgcact    4620
ttttatacta cagattggga tatcgataat attgcgtaaa aaatccttt ttttaaaaagc    4680 ttgtttacag taacgtaaat gaccagaaat cagatgaaaa tcacaagaaa gcaaataatt    4740
```

```
cacgttaaat cctgatatgt ttgattttgt gatgaaatca tggatgttca taggaattgt    4800
tgaaattgcg cttttttaac gaaatataca agtatcctgg agcttactta attaattaat    4860
gaatctttgt ttctagtttt acccatcgta aagatcttga gagctctcca ctttgaacct    4920
ctaacctagc gagggtttta ccgtactcgc tatctcgctt tgcaaatcca caagcttct     4980 gtattacatc ataagaaagt agagtgggcg ctcattggaa atagcttacg tagctcagaa    5040
aacgaatggt gcgaagaaaa ggggctttgc tagaagctgc tcattatttg tctgattgga    5100
tagcgagcta tctgatagaa aactacgtaa ttccttggat cgcagttttc tccagtttct    5160
aatgctaact gacgcaaatg tgatgtaatg ggctgcgatc ataatgacat gagcaattgg    5220
acaagaagct ataaatacga gtccaagttc aacagtttaa tcattcaatt caattccaat    5280
caatttaatt gtcttaaata ttcaaaacat gtgaagcagg tgtcggtacc cggggatcct    5340
ctagagtcga cctgcagaat aaagcaacga actaaacgaa atttattgct tctaacttta    5400 acttttggc aagctatgat gttcacaagc tgtcatagct tattttacga tttcacccct    5460 atatatttt aatgagattt caatcacatt aaaatacatg tctttatttt tataggcagt     5520
ttgttcatgc atatatgtag ttttgtattt ccttcgaaca gccttaattg atgtagcagt    5580
tactttttaa tggaattgtg tagttgcctt gttaatttct cattacgaca aggttgtgtt    5640
gtgtaaatac tcttttcttt agtaaacaat acgcgtcata ctaagggtaa gtaccattat    5700
tatggtgtat cacttgtaac tttcagtaca gctaattctt cacatttacc aatagcaaac    5760
cggtctaaaa aacatctatt atgacaataa aaagctccga acttctgaaa agaatgactg    5820
catatgaatg tgaaattaaa aaaaatatca acactacttc ttaatgaatg tattactttg    5880
gttctaggaa aatcaaaatg atatagtatt acaaattaat caatatatta ttcagtgttg    5940
tttttgcatg ttaatatctc cctaagtggt tacaatctat tcactagt                5988
```

<210> SEQ ID NO 46
<211> LENGTH: 20
<212> TYPE: DNA
<213> ORGANISM: Artificial Sequence
<220> FEATURE:
<223> OTHER INFORMATION: Description of Artificial Sequence: Forward
      primer

<400> SEQUENCE: 46
atggctgcgg agtcaatgag                                                  20

<210> SEQ ID NO 47
<211> LENGTH: 23
<212> TYPE: DNA
<213> ORGANISM: Artificial Sequence
<220> FEATURE:
<223> OTHER INFORMATION: Description of Artificial Sequence: Reverse
      primer

<400> SEQUENCE: 47
ttacttgtac agctcgtcca tgc                                              23

<210> SEQ ID NO 48
<211> LENGTH: 20
<212> TYPE: DNA
<213> ORGANISM: Artificial Sequence
<220> FEATURE:
<223> OTHER INFORMATION: Description of Artificial Sequence: Forward
      primer

<400> SEQUENCE: 48
gagtatgtgt acgagttgtc                                        20

<210> SEQ ID NO 49
<211> LENGTH: 21
<212> TYPE: DNA
<213> ORGANISM: Artificial Sequence
<220> FEATURE:
<223> OTHER INFORMATION: Description of Artificial Sequence: Reverse
      primer

<400> SEQUENCE: 49
tagcagcgaa tccaaaccat c                                      21

<210> SEQ ID NO 50
<211> LENGTH: 56
<212> TYPE: DNA
<213> ORGANISM: Artificial Sequence
<220> FEATURE:
<223> OTHER INFORMATION: Description of Artificial Sequence: Forward
      primer

<400> SEQUENCE: 50
ggcatggacg agctgtacaa gtaaaataaa gcaacgaact aaacgaaatt tattgc     56

<210> SEQ ID NO 51
<211> LENGTH: 53
<212> TYPE: DNA
<213> ORGANISM: Artificial Sequence
<220> FEATURE:
<223> OTHER INFORMATION: Description of Artificial Sequence: Reverse
      primer

<400> SEQUENCE: 51
taaagacaac tcgtacacat actcaccaaa gtaatacatt cattaagaag tag        53

<210> SEQ ID NO 52
<211> LENGTH: 51
<212> TYPE: DNA
<213> ORGANISM: Artificial Sequence
<220> FEATURE:
<223> OTHER INFORMATION: Description of Artificial Sequence: Reverse
      primer

<400> SEQUENCE: 52
taaagacaac tcgtacacat actctgctat tggtaaatgt gaagaattag c          51

<210> SEQ ID NO 53
<211> LENGTH: 50
<212> TYPE: DNA
<213> ORGANISM: Artificial Sequence
<220> FEATURE:
<223> OTHER INFORMATION: Description of Artificial Sequence: Reverse
      primer

<400> SEQUENCE: 53
taaagacaac tcgtacacat actcgaaaag agtatttaca caacacaacc            50

<210> SEQ ID NO 54
<211> LENGTH: 53
<212> TYPE: DNA
<213> ORGANISM: Artificial Sequence
<220> FEATURE:
<223> OTHER INFORMATION: Description of Artificial Sequence: Reverse
      primer

<400> SEQUENCE: 54

```
taaagacaac tcgtacacat actctcgaag gaaatacaaa actacatata tgc    53
```

<210> SEQ ID NO 55
<211> LENGTH: 42
<212> TYPE: DNA
<213> ORGANISM: Artificial Sequence
<220> FEATURE:
<223> OTHER INFORMATION: Description of Artificial Sequence: Reverse
      primer

<400> SEQUENCE: 55

```
taaagacaac tcgtacacat actcatgcat gaacaaactg cc    42
```

<210> SEQ ID NO 56
<211> LENGTH: 56
<212> TYPE: DNA
<213> ORGANISM: Artificial Sequence
<220> FEATURE:
<223> OTHER INFORMATION: Description of Artificial Sequence: Reverse
      primer

<400> SEQUENCE: 56

```
taaagacaac tcgtacacat actcataaag acatgtattt taatgtgatt gaaatc    56
```

<210> SEQ ID NO 57
<211> LENGTH: 53
<212> TYPE: DNA
<213> ORGANISM: Artificial Sequence
<220> FEATURE:
<223> OTHER INFORMATION: Description of Artificial Sequence: Reverse
      primer

<400> SEQUENCE: 57

```
taaagacaac tcgtacacat actctgaaat ctcattaaaa atatataagg gtg    53
```

<210> SEQ ID NO 58
<211> LENGTH: 48
<212> TYPE: DNA
<213> ORGANISM: Artificial Sequence
<220> FEATURE:
<223> OTHER INFORMATION: Description of Artificial Sequence: Reverse
      primer

<400> SEQUENCE: 58

```
taaagacaac tcgtacacat actcggtgaa atcgtaaaat aagctatg    48
```